(12) United States Patent
Hiraguchi et al.

(10) Patent No.: US 11,278,652 B2
(45) Date of Patent: Mar. 22, 2022

(54) HOLLOW FIBER MEMBRANE LAYER LAMINATE AND METHOD OF MANUFACTURING HOLLOW FIBER MEMBRANE LAYER LAMINATE

(71) Applicant: TERUMO KABUSHIKI KAISHA, Tokyo (JP)

(72) Inventors: Ryuji Hiraguchi, Elkton, MD (US); Akira Gyoten, Elkton, MD (US)

(73) Assignee: TERUMO KABUSHIKI KAISHA, Tokyo (JP)

(*) Notice: Subject to any disclaimer, the term of this patent is extended or adjusted under 35 U.S.C. 154(b) by 471 days.

(21) Appl. No.: 16/359,108

(22) Filed: Mar. 20, 2019

(65) Prior Publication Data
US 2019/0216999 A1    Jul. 18, 2019

Related U.S. Application Data

(63) Continuation of application No. PCT/JP2017/034957, filed on Sep. 27, 2017.

(30) Foreign Application Priority Data

Sep. 30, 2016    (JP) .............................. JP2016-194542

(51) Int. Cl.
*A61M 1/16*    (2006.01)
*A61M 1/36*    (2006.01)
*B01D 63/02*    (2006.01)

(52) U.S. Cl.
CPC ........ *A61M 1/1698* (2013.01); *A61M 1/1629* (2014.02); *A61M 1/3627* (2013.01);
(Continued)

(58) Field of Classification Search
CPC .............. A61M 1/1629; A61M 1/1698; A61M 1/3627; A61M 1/3633; A61M 2005/366;
(Continued)

(56) References Cited

U.S. PATENT DOCUMENTS 5,376,334 A * 12/1994 Haworth ................ B01D 63/02
                                                      210/321.87
6,638,479 B1    10/2003 Elgas et al.
(Continued)

FOREIGN PATENT DOCUMENTS

EP    2832385 A1    2/2015

OTHER PUBLICATIONS

Extended European Search Report, EP17856220, dated Feb. 14, 2020.
(Continued)

*Primary Examiner* — Benjamin J Klein
(74) *Attorney, Agent, or Firm* — MacMillan, Sobanski & Todd, LLC

(57)    ABSTRACT

A hollow fiber membrane laminate that includes a plurality of hollow fiber membranes wound to form a plurality of layers in a cylinder shape. The hollow fiber membranes are wound around a central axis while reciprocating a feeding point of the hollow fiber membranes along a central axis. Hollow fiber membranes adjacent to each other in each respective layer are separated by a predetermined separation distance. A speed differential z is reduced for successive layers approaching an outer side of the cylinder to maintain the predetermined separation distance. The speed differential z has a value obtained by dividing a pitch of the hollow fiber membranes within a respective layer by a traverse reciprocating distance.

8 Claims, 15 Drawing Sheets

(52) U.S. Cl.
CPC ......... *B01D 63/021* (2013.01); *B01D 63/025* (2013.01); *B01D 63/026* (2013.01); *A61M 1/3633* (2013.01); *A61M 2205/366* (2013.01); *A61M 2207/00* (2013.01)

(58) Field of Classification Search
CPC ............. A61M 2207/00; B01D 63/021; B01D 63/025; B01D 63/026; B01D 69/081; B01D 2313/38; B29C 53/665
See application file for complete search history.

(56) References Cited

U.S. PATENT DOCUMENTS

| | | |
|---|---|---|
| 6,824,679 B1 | 11/2004 | Dzengeleski et al. |
| 9,867,920 B2 | 1/2018 | Takeuchi et al. |
| 2006/0065588 A1 | 3/2006 | Koch et al. |
| 2012/0277653 A1 | 11/2012 | Olsen et al. |
| 2012/0277654 A1 | 11/2012 | Olson et al. |
| 2014/0030146 A1 | 1/2014 | Takeuchi |
| 2015/0010433 A1* | 1/2015 | Takeuchi ................ F28D 7/103 422/48 |
| 2016/0331882 A1 | 11/2016 | Saito |

OTHER PUBLICATIONS

International Search Report, PCT/JP2017/034957, dated Dec. 20, 2017.
Translation of PCT Written Opinion, PCT/JP2017/034957, dated Jan. 9, 2018.

* cited by examiner

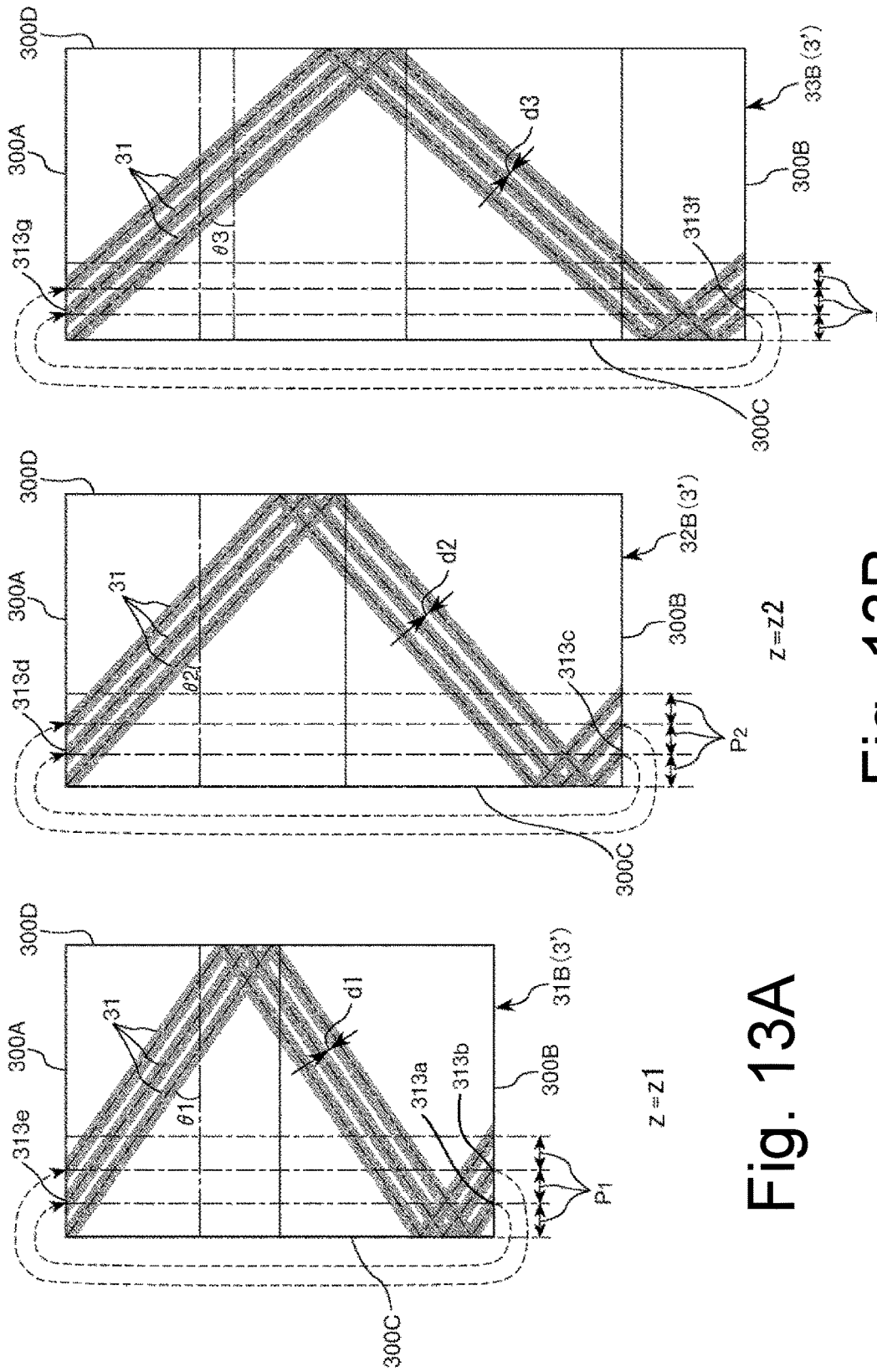

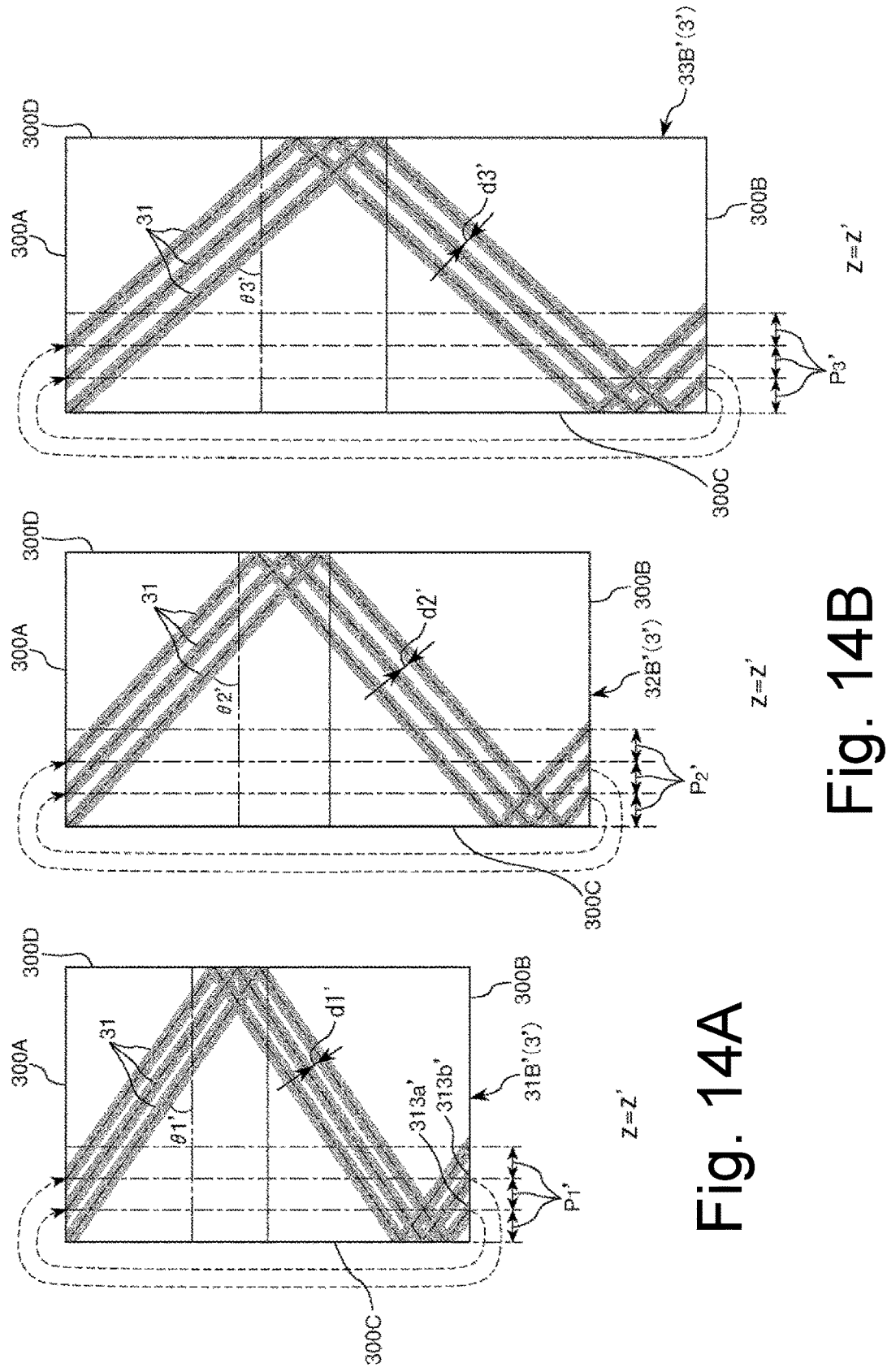

ical axis of the cylinder while reciprocating the hollow fiber membranes in a central axis direction of the cylinder to laminate, in a radial direction of the cylinder, the hollow fiber membrane layers in each of which the hollow fiber membranes adjacent to each other in the central axial direction of the cylinder are separated by a predetermined distance. During the winding step, a speed differential z is reduced as the hollow fiber membrane layer approaches an outer side in the radial direction of the cylinder, wherein the speed differential z is a value obtained by dividing a pitch between the hollow fiber membranes adjacent to each other in the central axis direction of the cylinder by a traverse reciprocating distance.

HOLLOW FIBER MEMBRANE LAYER LAMINATE AND METHOD OF MANUFACTURING HOLLOW FIBER MEMBRANE LAYER LAMINATE

CROSS REFERENCE TO RELATED APPLICATIONS

This application is a continuation of PCT Application No. PCT/JP2017/034957, filed Sep. 27, 2017, based on and claiming priority to Japanese Application No. 2016-194542, filed Sep. 30, 2016, both of which are incorporated herein by reference in their entirety.

BACKGROUND OF THE INVENTION

The present invention relates to a method of manufacturing a hollow fiber membrane layer laminate and to a hollow fiber membrane layer laminate.

In the related art, heat exchangers or oxygenators having a hollow fiber membrane layer laminate which is configured to have a plurality of hollow fiber membranes and has a cylinder shape as a whole shape are known (for example, U.S. Pat. No. 9,867,920).

A hollow fiber membrane layer laminate disclosed in U.S. Pat. No. 9,867,920 is formed by winding a plurality of hollow fiber membranes around a central axis of a cylinder in a state where each hollow fiber is tilted with respect to the central axis of the cylinder while reciprocating the plurality of hollow fiber membranes in a central axis direction of the cylinder.

As the winding of the hollow fiber membranes proceeds, the outer diameter of the cylinder increases. Therefore, in a case where the hollow fiber membrane is fed in a constant amount and reciprocated at a constant speed, the separation distance between hollow fiber membranes adjacent to each other in the central axis direction of the cylinder differs between the inner side of the cylinder, namely, the winding start, and the outer side of the cylinder, namely, the winding end. For example, even if hollow fiber membranes are wound with an appropriate separation distance at the winding start, the separation distance between hollow fiber membranes adjacent to each other becomes larger at the winding end. Meanwhile, in order to have an appropriate separation distance at the winding end, the separation distance at the winding start needs to be reduced more than necessary in winding hollow fiber membranes. In the former case, the blood loading amount is large, which places a high burden on patients. Meanwhile, in the latter case, air bubbles can remain between hollow fiber membranes adjacent to each other at the time of initial loading or the pressure loss in the blood flow path can become higher than necessary, which can also place a high burden on patients.

SUMMARY OF THE INVENTION

An object of the present invention is to provide a hollow fiber membrane layer laminate and a method of manufacturing a hollow fiber membrane layer laminate, which make it possible to reduce the blood loading amount, to prevent air bubbles from remaining between hollow fiber membranes, and to prevent the pressure loss in the blood flow path from increasing more than necessary.

The object is achieved by means of a method of manufacturing a hollow fiber membrane layer laminate that includes a plurality of hollow fiber membranes forming a laminate of a plurality of hollow fiber membrane layers and has a cylinder shape. The hollow fiber membranes are wound around a central axis of the cylinder while recipro- In particular, a difference between the speed differentials z in the hollow fiber membrane layers adjacent to each other in the radial direction of the cylinder is preferably within a range of 0.4% to 1.1% of the speed differential z of the hollow fiber membrane layer on an inner side.

The invention further includes a hollow fiber membrane layer laminate including a plurality of hollow fiber membranes and having a cylinder shape. The plurality of hollow fiber membranes form a laminate of a plurality of hollow fiber membrane layers, wherein the laminated layers overlie each other in a radial direction of the cylinder. The hollow fiber membranes within each layer have longitudinal side edges that are separated from each other by a predetermined separation distance. The predetermined separation distance between the hollow fiber membranes adjacent to each other in an innermost layer of the cylinder has substantially the same value as the separation distance between the hollow fiber membranes adjacent to each other in an outermost layer.

In a preferred hollow fiber membrane layer laminate, the predetermined separation distance between hollow fiber membranes adjacent to each other in the same layer is from 50 μm to 300 μm.

In a preferred hollow fiber membrane layer laminate, the hollow fiber membranes have an outer diameter of 300 μm to 1,000 μm.

The hollow fiber membrane layer laminate may preferably be used as a heat exchanger in which a heat medium passes through the inside the hollow fiber membranes.

According to the present invention, in the winding step, the speed differential z is reduced as the hollow fiber membrane layer approaches the outer side. Therefore, the separation distance between hollow fiber membranes adjacent to each other in the same and adjacent layers can be prevented from excessively changing as the hollow fiber membrane layer approaches the outer side. As a result, an excessive increase in the blood loading amount can be prevented, air bubbles can be prevented from remaining between hollow fiber membranes, and the pressure loss in the blood flow path can be prevented from increasing more than necessary.

BRIEF DESCRIPTION OF THE DRAWINGS

FIGS. 13A, 13B, and 13C are development views illustrating a winding step in the method of manufacturing a hollow fiber membrane layer laminate of the present invention, wherein FIGS. 13A, 13B, and 13C illustrate successive layers being formed, radially atop one another.

FIGS. 14A, 14B, and 14C are development views illustrating the formation of successive radial layers during a winding step as known in the prior art.

DETAILED DESCRIPTION OF PREFERRED EMBODIMENTS

Figure 1:
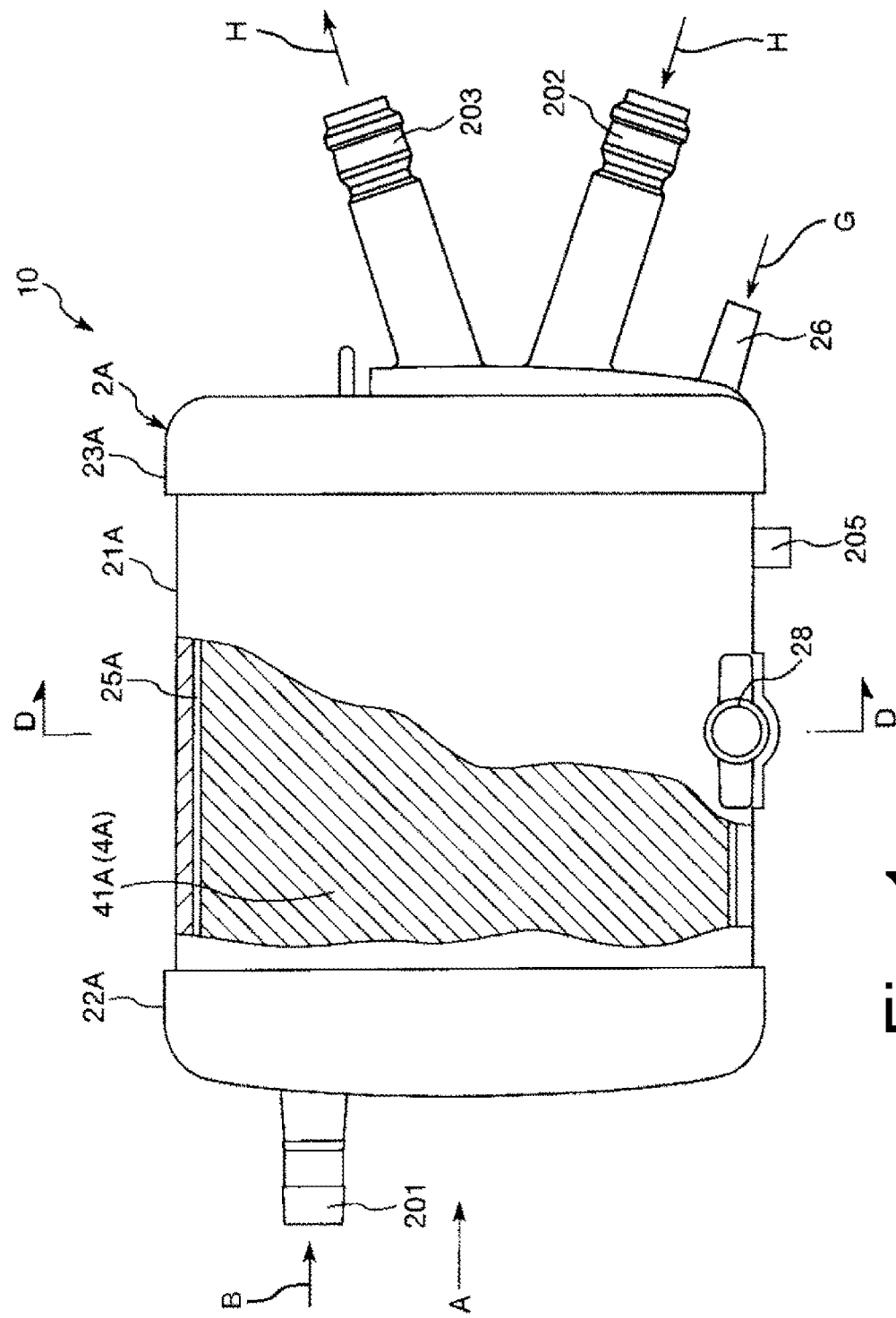
FIG. 1 is a plan view of an oxygenator internally including a hollow fiber membrane layer laminate of the present invention.
Figure 2:
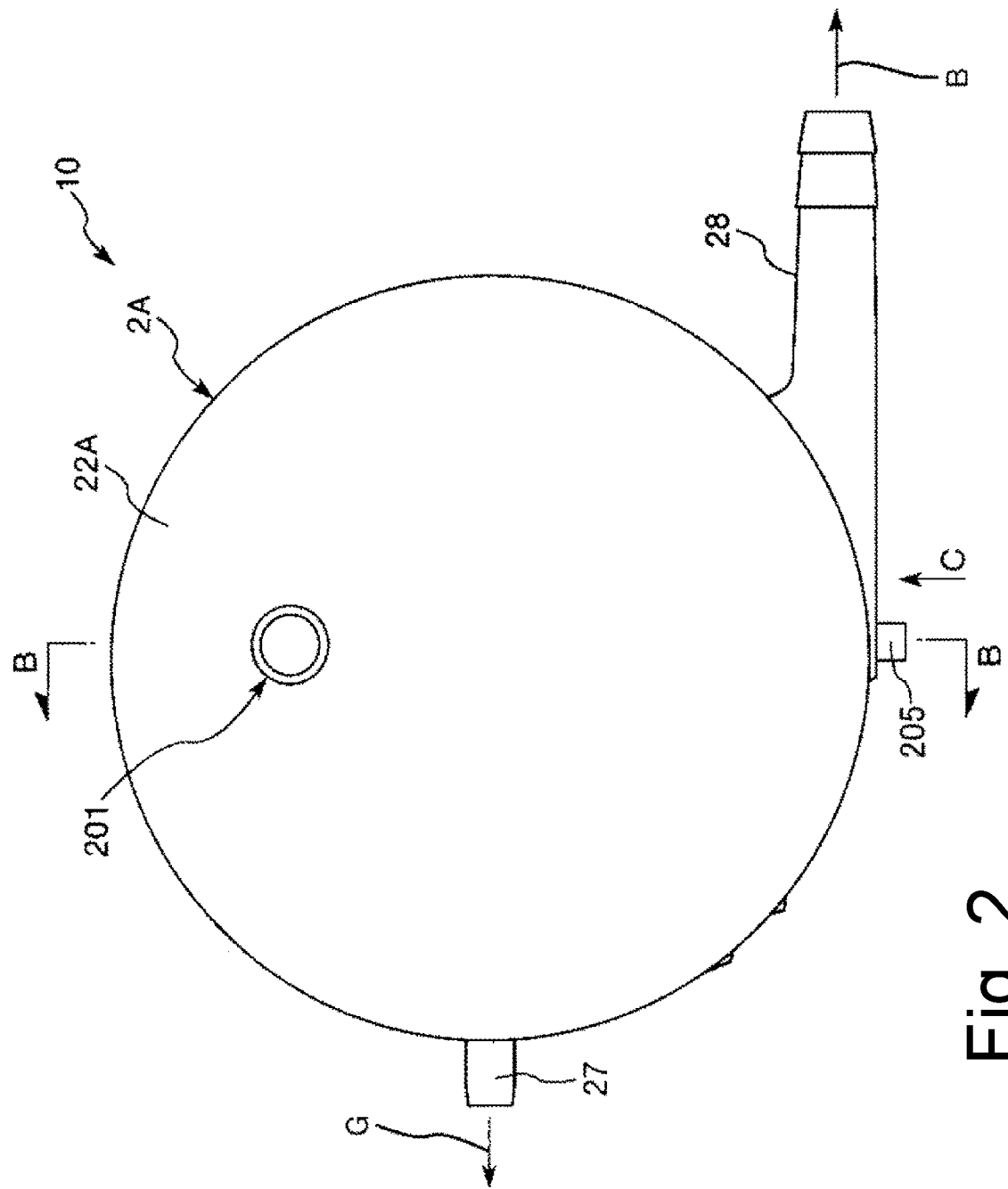
FIG. 2 is a view of the hollow fiber membrane layer laminate illustrated in FIG. 1 seen in the direction of an arrow A.

Hereinafter, a method of manufacturing a hollow fiber membrane layer laminate of the present invention and the method of manufacturing a hollow fiber membrane layer laminate will be described in detail based on a preferable embodiment illustrated in the accompanying drawings.

Note that, the left sides in FIGS. 1, 3, 4, 7 to 10, and 12 to 14 will be referred to as "left" or "leftward (one side)" and the right sides therein will be referred to as "right" or "rightward (the other side)". In addition, in FIGS. 1 to 6, the inner side of the oxygenator will be described as "blood inflow side" or "upstream side" and the outer side thereof will be described as "blood outflow side" or "downstream side".

An oxygenator 10 illustrated in FIGS. 1 to 5 has a substantially cylindrical (i.e., columnar) shape. This oxygenator 10 is an oxygenator which is equipped with a heat exchanger and includes a heat exchange section 10B that is provided on the inner side and performs heat exchange with respect to blood, and an oxygenator section 10A that is provided on an outer circumferential side of the heat exchange section 10B and serves as a gas exchange section performing gas exchange with respect to blood. For example, the oxygenator 10 is used by being installed in an extracorporeal blood circulation loop.

The oxygenator 10 has a housing 2A, and the oxygenator section 10A and the heat exchange section 10B are accommodated inside the housing 2A.

The housing 2A is configured to have a cylindrical housing main body 21A, a disk-shaped first lid 22A which seals a left end opening of the cylindrical housing main body 21A, and a disk-shaped second lid 23A which seals a right end opening of the cylindrical housing main body 21A.

The cylindrical housing main body 21A, the first lid 22A, and the second lid 23A are formed of a resin material. The first lid 22A and the second lid 23A are fixedly attached to the cylindrical housing main body 21A by a method such as welding and bonding which is performed by using an adhesive.

A pipe-shaped blood outflow port 28 is formed in an outer peripheral portion of the cylindrical housing main body 21A. The blood outflow port 28 protrudes substantially in a tangential direction of an outer peripheral surface of the cylindrical housing main body 21A (refer to FIG. 5).

A pipe-shaped purge port 205 is protrusively formed in the outer peripheral portion of the cylindrical housing main body 21A. The purge port 205 is formed in the outer peripheral portion of the cylindrical housing main body 21A such that a central axis thereof intersects a central axis of the cylindrical housing main body 21A.

A pipe-shaped gas outflow port 27 is protrusively formed in the first lid 22A. The gas outflow port 27 is formed in the outer peripheral portion of the first lid 22A such that the central axis intersects the center of the first lid 22A (refer to FIG. 2).

In addition, a blood inflow port 201 protrudes from an end surface of the first lid 22A such that a central axis thereof becomes eccentric with respect to the center of the first lid 22A.

A pipe-shaped gas inflow port 26, a heat medium inflow port 202, and a heat medium outflow port 203 are protrusively formed in the second lid 23A. The gas inflow port 26 is formed at an edge portion on the end surface of the second lid 23A. Each of the heat medium inflow port 202 and the heat medium outflow port 203 is formed substantially in a central portion on the end surface of the second lid 23A. In addition, each of the central axes of the heat medium inflow port 202 and the heat medium outflow port 203 is slightly tilted with respect to the central axis of the second lid 23A.

Note that, in the present invention, the whole shape of the housing 2A is not necessarily a completely columnar shape. For example, the housing 2A may have a shape partially lacking, a shape to which a variant portion is added, or the like.

Figure 3:
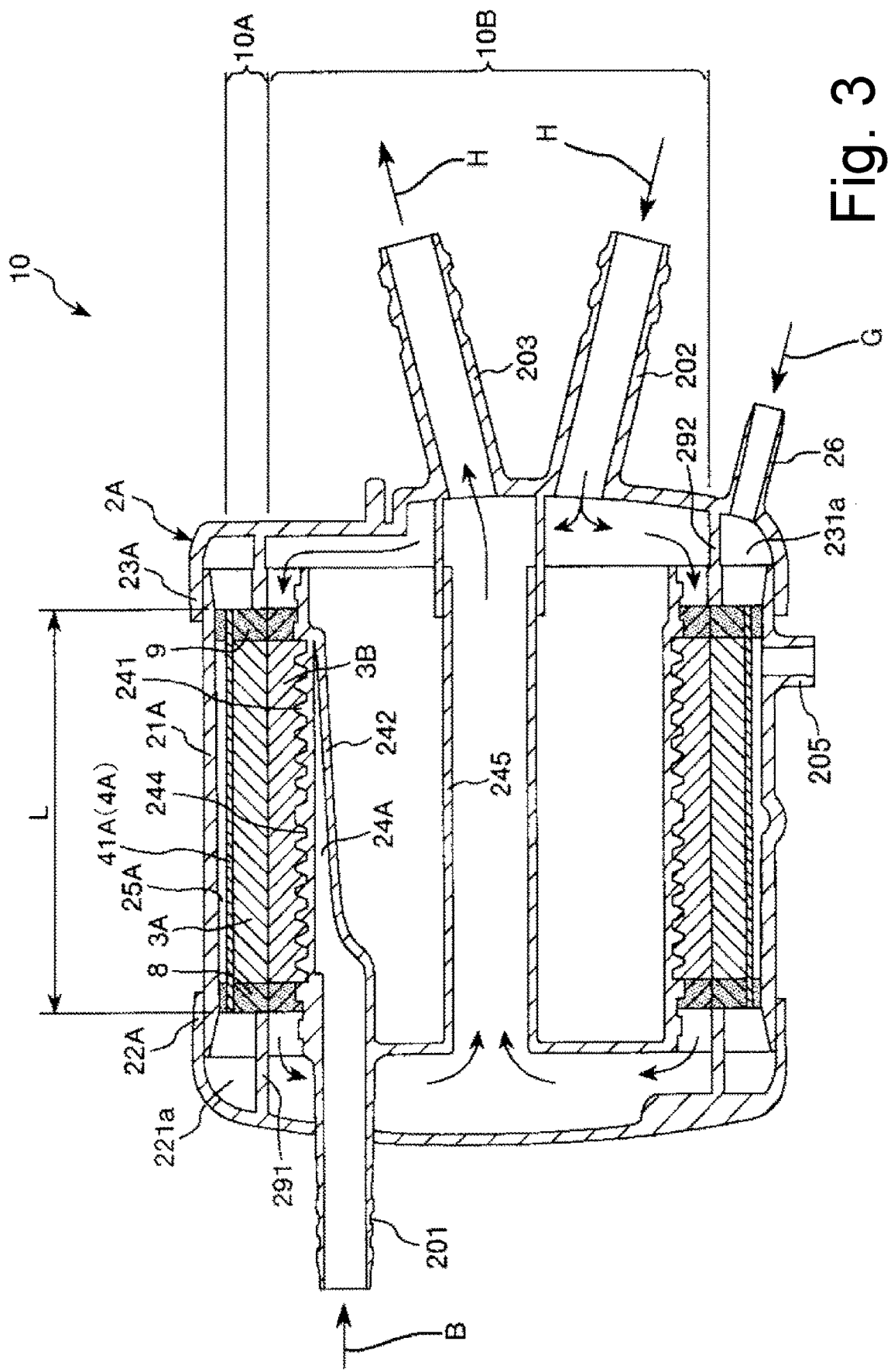
FIG. 3 is a cross-sectional view taken along line B-B in FIG. 2.
Figure 4:
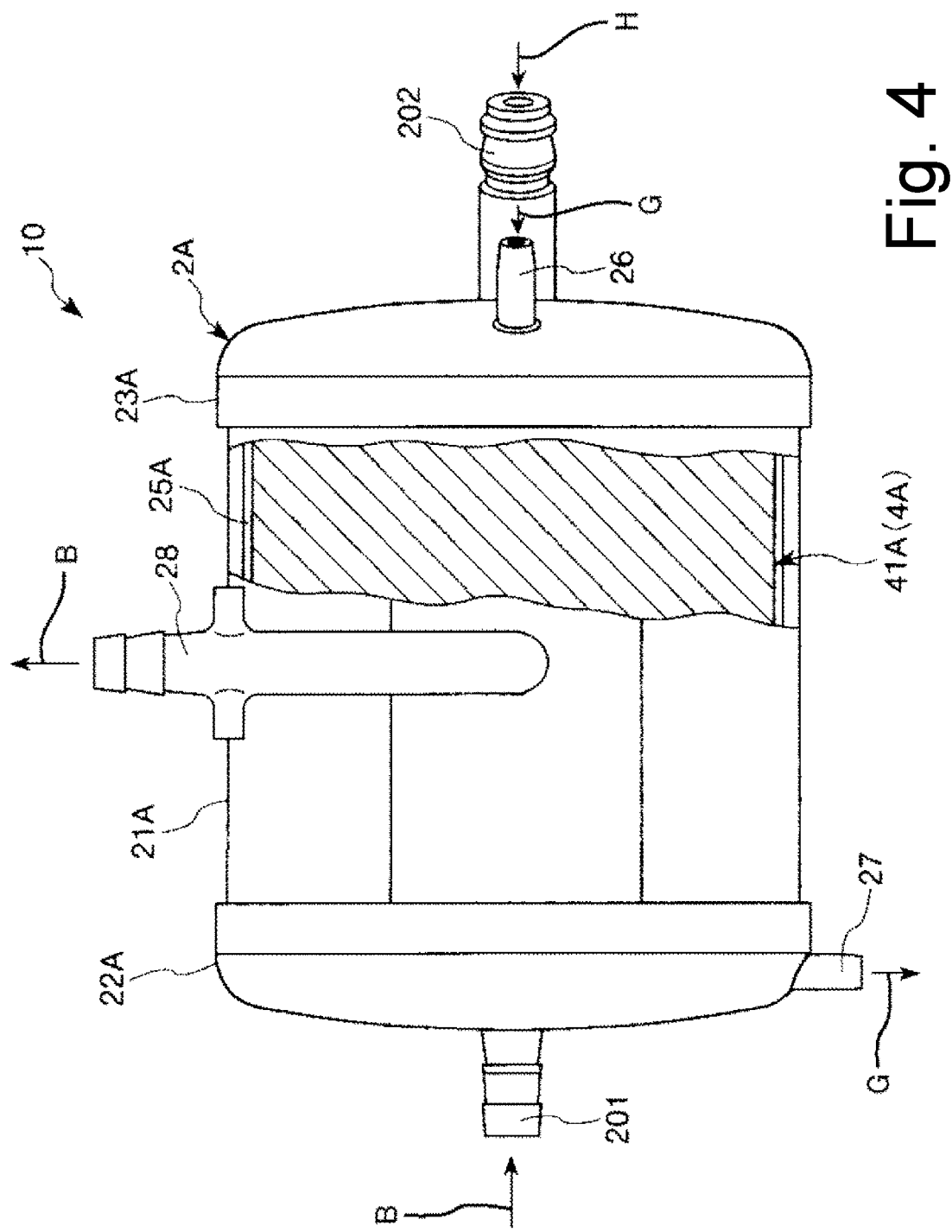
FIG. 4 is a view seen in the direction of an arrow C in FIG. 2.
Figure 5:
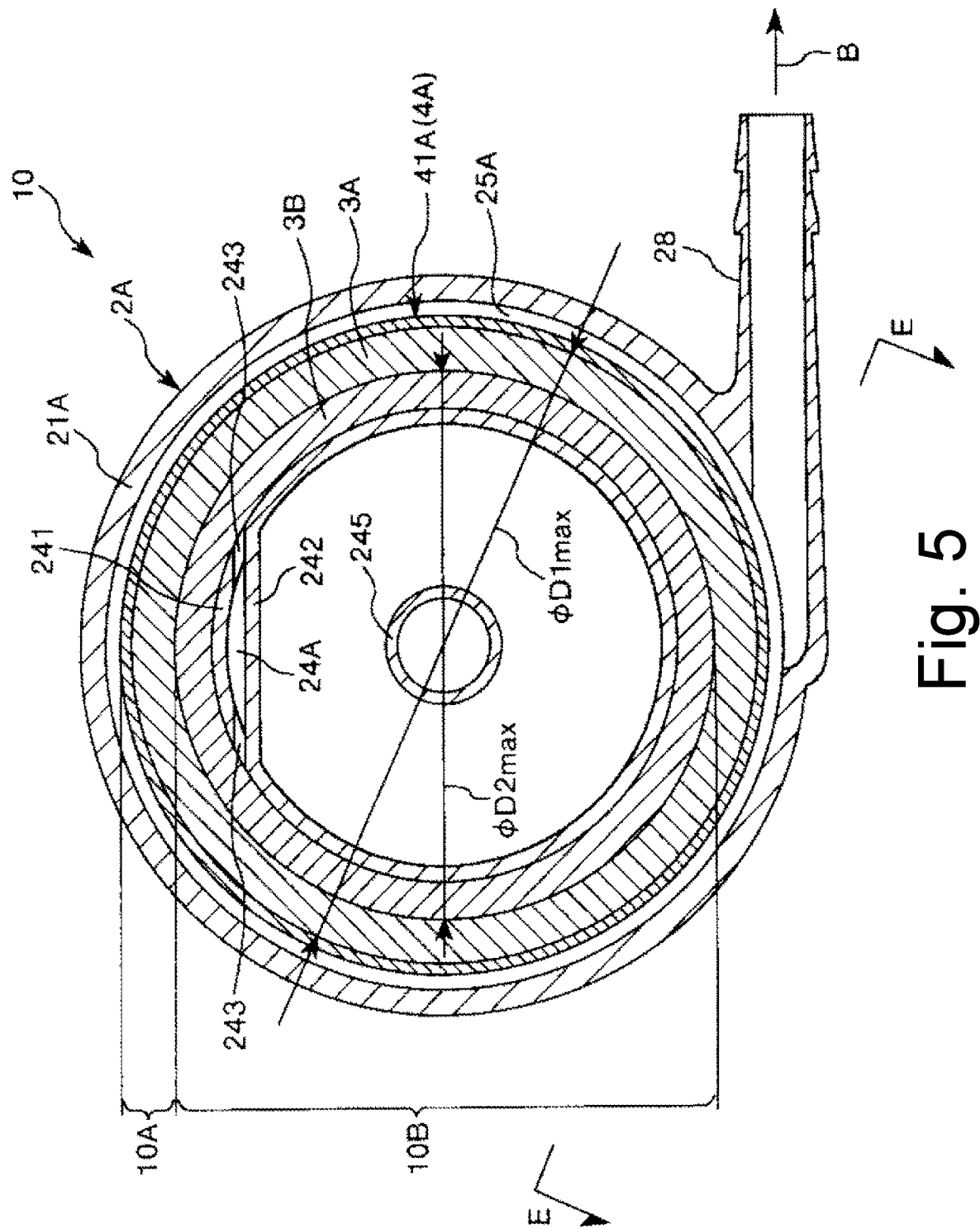
FIG. 5 is a cross-sectional view taken along line D-D in FIG. 1.

As illustrated in FIGS. 3 and 5, the oxygenator section 10A having a cylindrical shape along an inner peripheral surface thereof is accommodated inside the housing 2A. The oxygenator section 10A is configured to have a cylindrical hollow fiber membrane layer laminate 3A and a filter member 41A which serves as air bubble removal means 4A provided on the outer circumferential side of the hollow fiber membrane layer laminate 3A. The hollow fiber membrane layer laminate 3A and the filter member 41A are disposed in the order of the hollow fiber membrane layer laminate 3A and the filter member 41A from the blood inflow side.

In addition, the heat exchange section 10B having a cylindrical shape along the inner peripheral surface thereof is installed on the inner side of the oxygenator section 10A. The heat exchange section 10B has a hollow fiber membrane layer laminate 3B.

Figure 6:
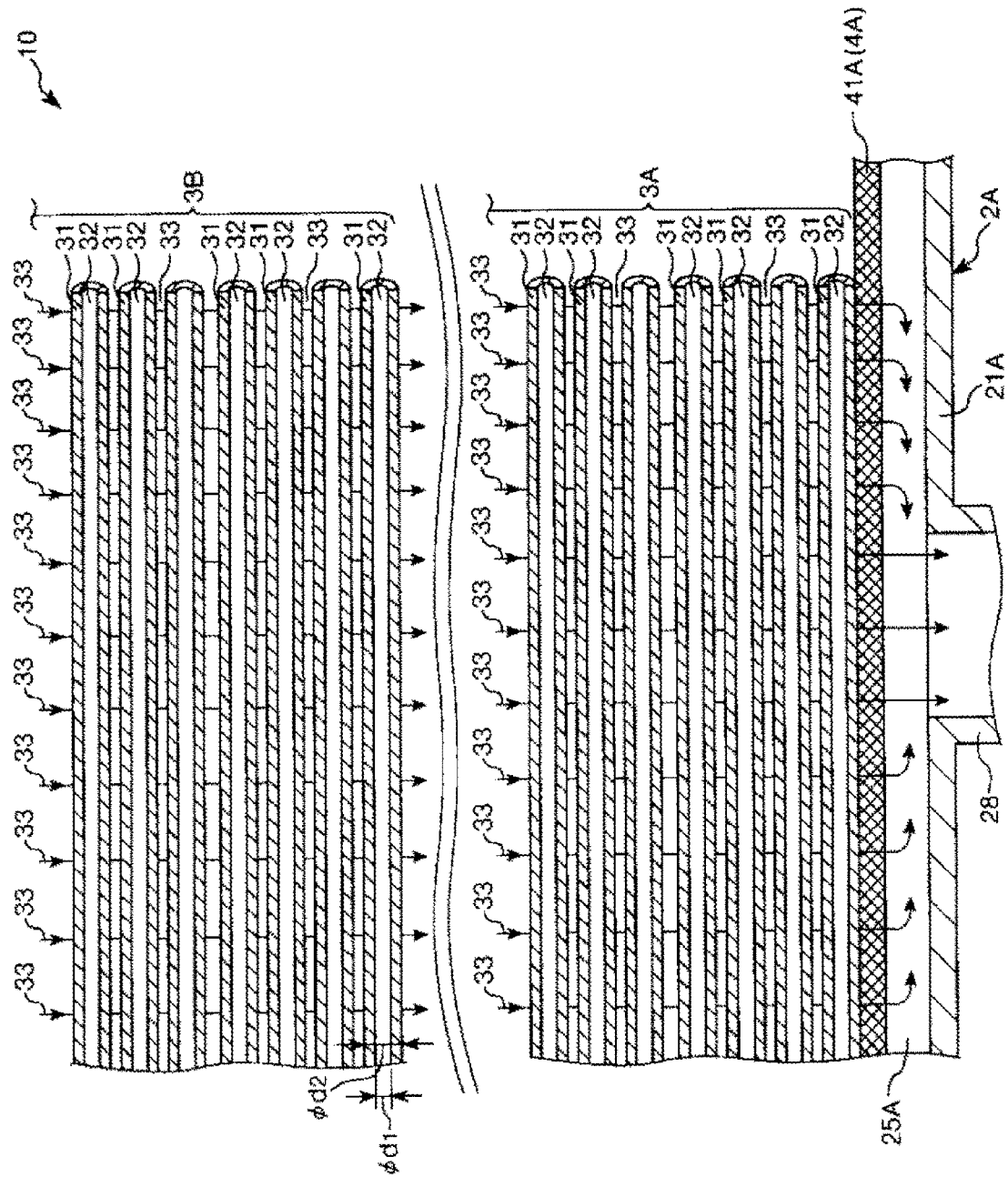
FIG. 6 is a cross-sectional view taken along line E-E in FIG. 5.

As illustrated in FIG. 6, each of the hollow fiber membrane layer laminated bodies 3A and 3B is configured to have a plurality of hollow fiber membranes 31 and is formed by integrating and laminating these hollow fiber membranes 31 in a layered manner. The number of laminated layers is not particularly limited. For example, it is preferable to be within a range of two layers to 40 layers. Note that, each of the hollow fiber membranes 31 of the hollow fiber membrane layer laminate 3A has a function of exchanging gas. Meanwhile, each of the hollow fiber membranes 31 of the hollow fiber membrane layer laminate 3B has a function of exchanging heat.

As illustrated in FIG. 3, both end portions of each of the hollow fiber membrane layer laminated bodies 3A and 3B are collectively fixed to an inner surface of the cylindrical housing main body 21A by a partition wall 8 and a partition wall 9. For example, the partition wall 8 and the partition wall 9 are constituted of a potting material such as polyurethane and silicone rubber, an adhesive, or the like. Moreover, an inner peripheral portion of the hollow fiber membrane layer laminate 3B engages with an uneven portion 244 formed in the outer peripheral portion of a first cylinder member 241. Due to the engagement and the state of being fixed by the partition wall 8 and the partition wall 9, the hollow fiber membrane layer laminate 3B is reliably fixed to the cylindrical housing main body 21A. Thus, it is possible to reliably prevent positional deviation of the hollow fiber membrane layer laminate 3B while the oxygenator 10 is in use. In addition, the uneven portion 244 also functions as a flow path for causing blood B to circumambulate the hollow fiber membrane layer laminate 3B in its entirety.

Note that, as illustrated in FIG. 5, for example, a maximum outer diameter $\phi D1_{max}$ of the hollow fiber membrane layer laminate 3A is preferably within a range of 20 mm to 200 mm and is more preferably within a range of 40 mm to 150 mm. A maximum outer diameter $\phi D2_{max}$ of the hollow fiber membrane layer laminate 3B is preferably within a range of 10 mm to 150 mm and is more preferably within a range of 20 mm to 100 mm. In addition, as illustrated in FIG. 3, lengths L of the hollow fiber membrane layer laminated bodies 3A and 3B in a central axis direction are preferably within a range of 30 mm to 250 mm and are more preferably within a range of 50 mm to 200 mm. In such conditions, the hollow fiber membrane layer laminate 3A has an excellent function of exchanging gas, and the hollow fiber membrane layer laminate 3B has an excellent function of exchanging heat.

A blood flow path 33 in which the blood B flows from the upper side toward the lower side in FIG. 6 is formed on the outer side of each of the hollow fiber membranes 31 between the partition wall 8 and the partition wall 9 inside the housing 2A, that is, in a gap between the hollow fiber membranes 31.

A blood inflow side space 24A which serves as a blood inflow portion for the blood B flowed in through the blood inflow port 201 and communicates with the blood inflow port 201 is formed on the upstream side of the blood flow path 33 (refer to FIGS. 3 and 5).

The blood inflow side space 24A is a space defined by the cylindrical first cylinder member 241 and a plate piece 242 which is disposed on the inner side of the first cylinder member 241 and is disposed to face a part of the inner peripheral portion thereof. The blood B which has flowed into the blood inflow side space 24A can flow down through the blood flow path 33 in its entirety via a plurality of side holes 243 formed in the first cylinder member 241.

In addition, a second cylinder member 245 disposed concentrically with the first cylinder member 241 is disposed on the inner side of the first cylinder member 241. As illustrated in FIG. 3, a heat medium H (for example, water) which has flowed in through the heat medium inflow port 202 sequentially passes through a flow path (hollow portion) 32 of each of the hollow fiber membranes 31 of the hollow fiber membrane layer laminate 3B on the outer circumferential side of the first cylinder member 241, and the inner side of the second cylinder member 245, thereby being discharged through the heat medium outflow port 203. In addition, when the heat medium H passes through the flow path 32 of each of the hollow fiber membranes 31, heat exchange (heating or cooling) is performed between the heat medium H and the blood B coming into contact with the hollow fiber membrane 31 inside the blood flow path 33.

The filter member 41A which has a function of capturing air bubbles present in the blood B flowing in the blood flow path 33 is disposed on the downstream side of the blood flow path 33.

The filter member 41A is constituted of a substantially rectangular sheet-like member (which will hereinafter be simply referred to as "a sheet") and is formed by winding the sheet along the outer circumference of the hollow fiber membrane layer laminate 3A. Both end portions of the filter member 41A are also fixedly attached to the partition walls 8 and 9 respectively. Accordingly, the filter member 41A is fixed to the housing 2A (refer to FIG. 3). Note that, it is preferable that this filter member 41A is provided such that the inner peripheral surface comes into contact with the outer peripheral surface of the hollow fiber membrane layer laminate 3A and covers substantially the whole surface of the outer peripheral surface.

In addition, even if air bubbles are present in blood flowing in the blood flow path 33, the filter member 41A can capture the air bubbles (refer to FIG. 6). In addition, air bubbles captured by the filter member 41A are thrust due to a blood flow and enter the inside of each of the hollow fiber membranes 31 in the vicinity of the filter member 41A. As a result, the air bubbles are removed from the blood flow path 33.

In addition, a cylindrical gap is formed between the outer peripheral surface of the filter member 41A and the inner peripheral surface of the cylindrical housing main body 21A, and the gap forms a blood outflow side space 25A. A blood outflow portion is constituted of the blood outflow side space 25A and the blood outflow port 28 communicating with the blood outflow side space 25A. Since the blood outflow portion has the blood outflow side space 25A, a space for the blood B which has penetrated the filter member 41A and flows toward the blood outflow port 28 is ensured, and thus, the blood B can be smoothly discharged.

As illustrated in FIG. 3, a toric rib 291 is protrusively formed on the inner side of the first lid 22A. The first lid 22A, the rib 291, and the partition wall 8 define a first room 221a. The first room 221a is a gas outflow chamber from which gas G flows out. The left end opening of each of the hollow fiber membranes 31 of the hollow fiber membrane layer laminate 3A is open to the first room 221a and communicates therewith. In the oxygenator 10, a gas outflow portion is constituted of the gas outflow port 27 and the first room 221a. Meanwhile, a toric rib 292 is protrusively formed on the inner side of the second lid 23A as well. The second lid 23A, the rib 292, and the partition wall 9 define a second room 231a. The second room 231a is a gas inflow chamber to which the gas G flows in. The right end opening of each of the hollow fiber membranes 31 of the hollow fiber membrane layer laminate 3A is open to the second room 231a and communicates therewith. In the oxygenator 10, a gas inflow portion is constituted of the gas inflow port 26 and the second room 231a.

A flow of blood in the oxygenator 10 of the present embodiment will now be described. In the oxygenator 10, the blood B which has flowed in through the blood inflow port 201 sequentially passes through the blood inflow side space 24A and the side hole 243, thereby flowing into the heat exchange section 10B. In the heat exchange section 10B, while flowing in the blood flow path 33 in a downstream direction, the blood B comes into contact with an outer surface of each of the hollow fiber membranes 31 of the heat exchange section 10B such that heat exchange (heating or cooling) is performed. The blood B subjected to heat exchange as described above flows into the oxygenator section 10A.

In the oxygenator section 10A, the blood B further flows in the blood flow path 33 in the downstream direction. Meanwhile, gas (gas including oxygen) supplied through the gas inflow port 26 is distributed from the second room 231a to the flow path 32 of each of the hollow fiber membranes 31 of the oxygenator section 10A and flows in the flow paths 32. Thereafter, the gas is integrated in the first room 221a and is discharged through the gas outflow port 27. The blood B flowing in the blood flow path 33 comes into contact with the outer surface of each of the hollow fiber membranes 31 of the oxygenator section 10A. Then, gas exchange, that is, oxygenation and decarbonation, is performed between the flow paths 32 and the gas G flowing therein.

In a case where air bubbles are intermixed in the blood B subjected to gas exchange, the air bubbles are captured by the filter member 41A, thereby being prevented from flowing out to the downstream side of the filter member 41A.

After heat exchange and gas exchange are sequentially performed and air bubbles are removed, the blood B flows out through the blood outflow port 28.

As described above, both the hollow fiber membrane layer laminate 3A and the hollow fiber membrane layer laminate 3B are configured to have a plurality of hollow fiber membranes 31. The hollow fiber membrane layer laminate 3A and the hollow fiber membrane layer laminate 3B are different from each other in ranges of the purpose, the material (the microstructure of a resin, and the like), the dimensions, and the like. In addition, the present invention is particularly effective at the hollow fiber membrane layer laminate 3B constituting a heat exchange section (which will be described below). Therefore, hereinafter, the hollow fiber membrane layer laminate 3B will be representatively described.

An inner diameter $\phi d_1$ of the hollow fiber membrane 31 is preferably within a range of 50 μm to 700 μm and is more preferably within a range of 70 μm to 600 μm (refer to FIG. 6). An outer diameter $\phi d_2$ of the hollow fiber membrane 31 is preferably within a range of 300 μm to 1,000 μm and is more preferably within a range of 400 μm to 900 μm (refer to FIG. 6). Accordingly, the effects of the present invention can be remarkably obtained as described below.

Moreover, a ratio $d_1/d_2$ between the inner diameter $\phi d_1$ and the outer diameter $\phi d_2$ is preferably within a range of 0.5 to 0.9 and is more preferably within a range of 0.6 to 0.85. In each of the hollow fiber membranes 31 having such conditions, while retaining its own strength, a pressure loss caused when the gas G flows in the flow path 32 which is the hollow portion of the hollow fiber membrane 31 can be relatively reduced. Furthermore, it contributes to maintaining the winding state of the hollow fiber membrane 31. For example, if the inner diameter $\phi d_1$ is larger than the foregoing upper limit value, the thickness of the hollow fiber membrane 31 becomes thin, and the strength is deteriorated depending on other conditions. In addition, if the inner diameter $\phi d_1$ is smaller than the foregoing lower limit value, a pressure loss caused when the gas G flows in the hollow fiber membrane 31 increases depending on other conditions.

In addition, the separation distance between the hollow fiber membranes 31 adjacent to each other is preferably within a range of 50 μm to 300 μm and is more preferably within a range of 100 μm to 250 μm. Accordingly, the effects of the present invention can be remarkably obtained as described below.

The method of manufacturing a hollow fiber membrane 31 is not particularly limited. Examples thereof include a method of using extrusion molding, and other methods such as a stretching method and a solid-liquid phase separation method. The hollow fiber membrane 31 having a predetermined inner diameter $\phi d_1$ and a predetermined outer diameter $\phi d_2$ can be manufactured by this method.

For example, as a constituent material of each of the hollow fiber membranes 31, a hydrophobic polymer material such as polypropylene, polyethylene, polysulfone, polyacrylonitrile, polytetrafluoroethylene, polymethylpentene, or polyamide is used. A polyolefin resin is preferably used, and polypropylene is more preferably used. Selecting such resin materials contributes to maintaining the winding state of the hollow fiber membrane 31 and also contributes to the cost reduction at the time of manufacturing.

The hollow fiber membrane layer laminate 3B is obtained from a base material 3' in which a plurality of hollow fiber membranes 31 are integrated and are wound to have a shape of a cylinder as a whole shape. This base material 3' is manufactured in the middle of manufacturing performed by the manufacturing method of the present invention.

Separately from the winding of the hollow fiber membrane layer laminate 3B as explained above, the hollow fiber membrane layer laminate 3A is manufactured according to the same method, and then the oxygenator 10 is completed using laminates 3A and 3B. A preferred method relating to the manufacture of the hollow fiber membrane layer laminates and their assembly into an oxygenator includes a first step, a second step, a third step, a fourth step, a fifth step, and a sixth step. Next, these will be described.

<First Step (Winding Step)>

Figure 7A:
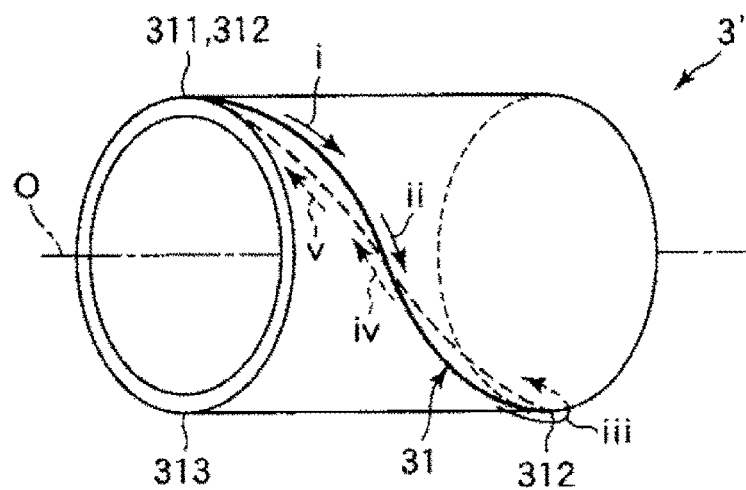
FIG. 7A is a perspective view and FIG. 7B is a development view illustrating a hollow fiber membrane layer laminate manufactured by a method of manufacturing a hollow fiber membrane layer laminate of the present invention.
Figure 7B:
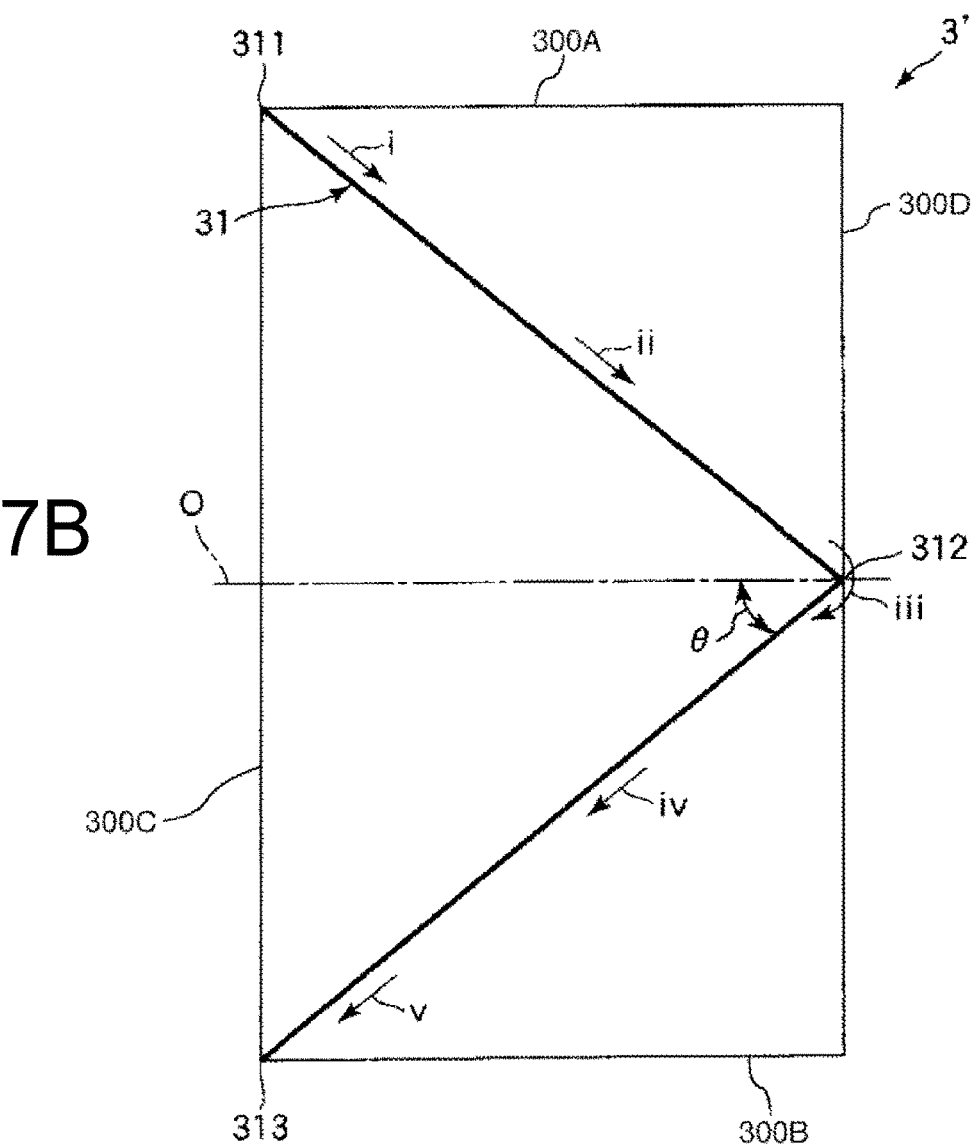

As illustrated in FIG. 7, the first step is a winding step in which a plurality of hollow fiber membranes 31 are wound to have a cylinder shape as a whole shape. Accordingly, the base material (primary base material) 3' is obtained. Note that, in FIG. 7 (the same applies to FIG. 12), one hollow fiber membrane 31 is representatively depicted.

Figure 9:
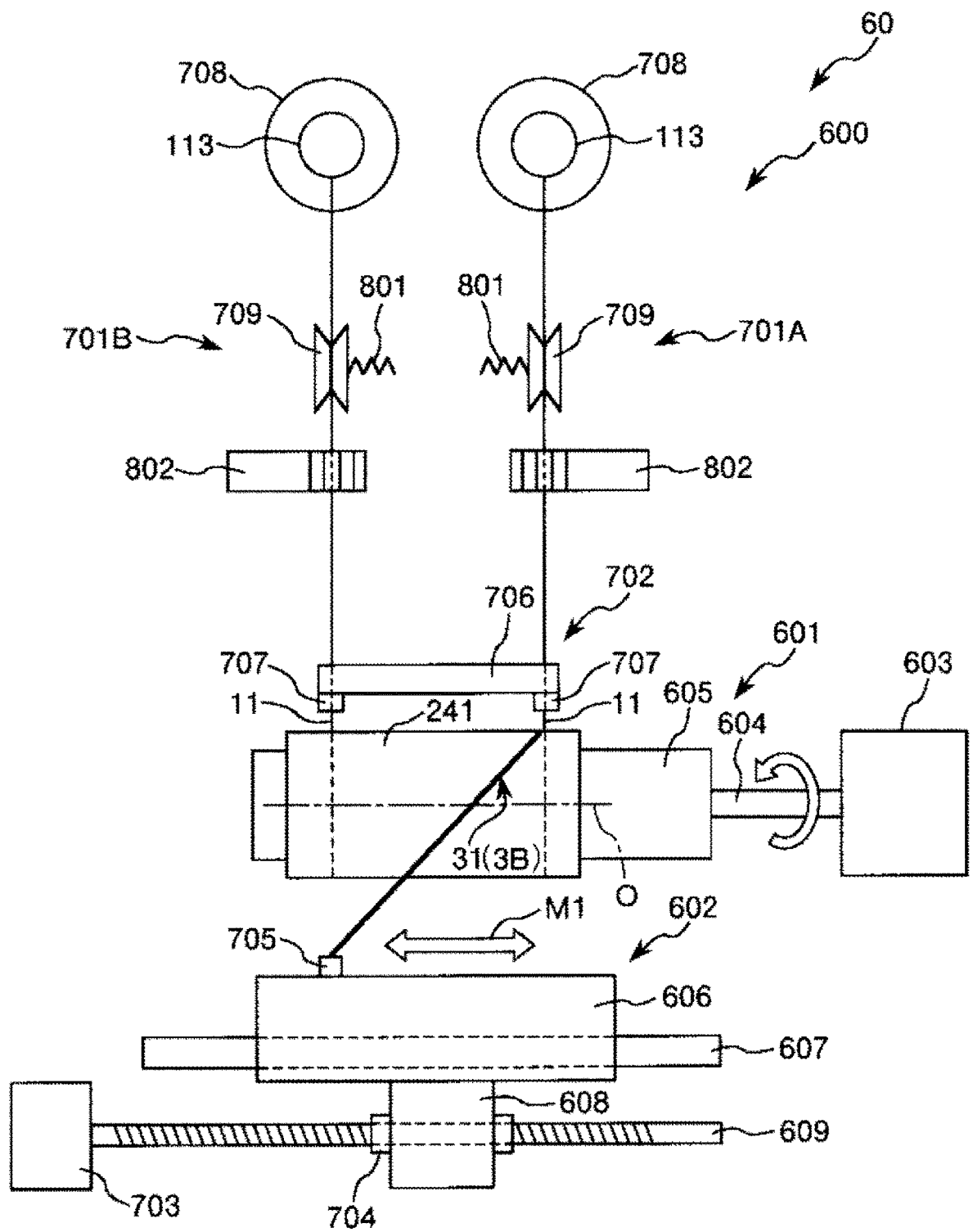
FIG. 9 is a view illustrating an apparatus used in the method of manufacturing a hollow fiber membrane layer laminate of the present invention.
Figure 10:
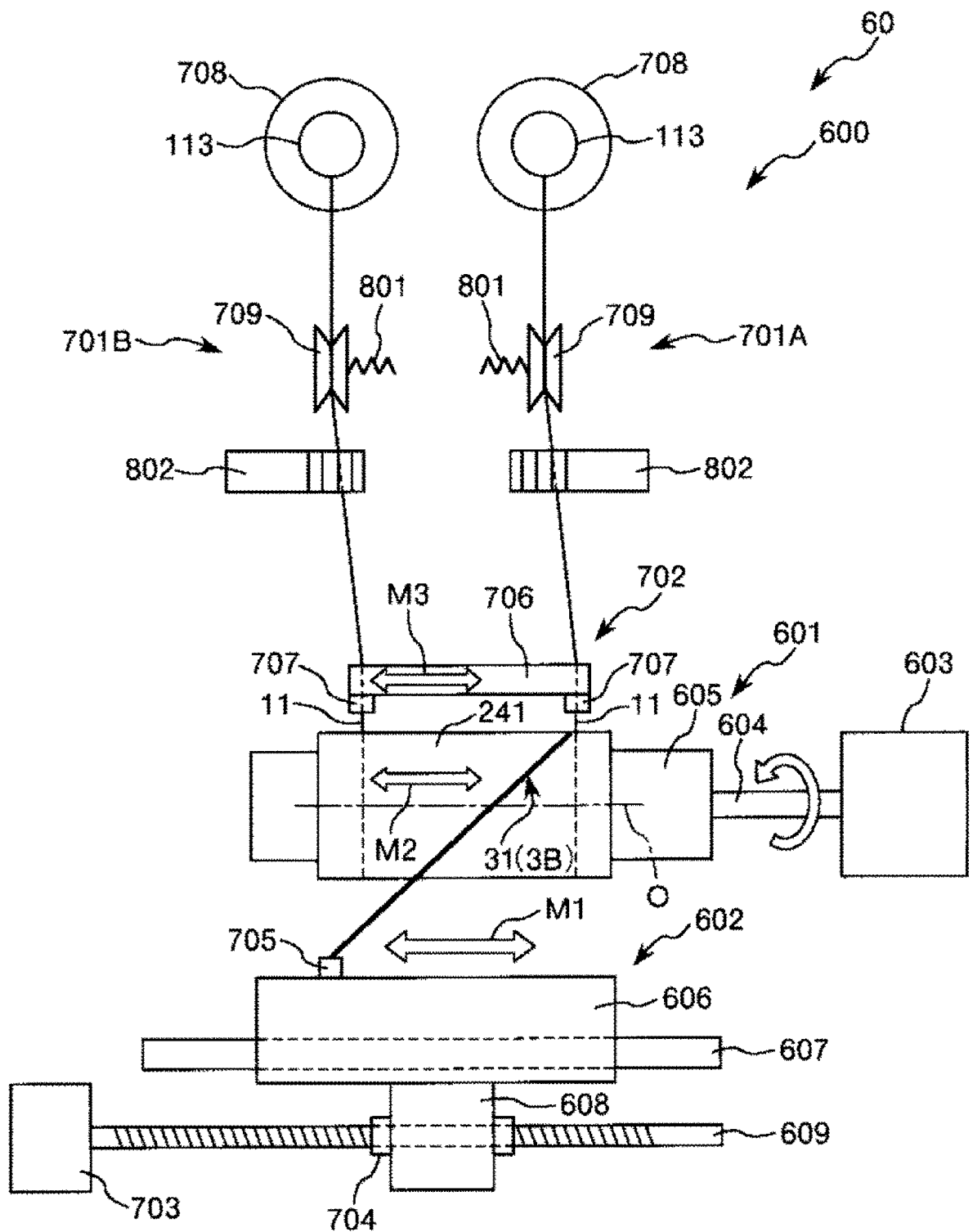
FIG. 10 is another view illustrating the apparatus used in the method of manufacturing a hollow fiber membrane layer laminate of the present invention.

In this first step, a winding apparatus 60 illustrated in FIGS. 9 and 10 is used. The winding apparatus 60 includes tubular core rotary means 601, a winding device 602, and a fixing device 600.

The tubular core rotary means 601 includes a motor 603, a motor shaft 604, and a core attachment member 605 which is fixed to the motor shaft 604. The first cylinder member 241 which is a part of the oxygenator 10 is attached to the core attachment member 605 and is rotated by the motor 603.

The winding device 602 is provided with a main body portion 606 including an accommodation portion which internally accommodates the hollow fiber membrane 31, and a discharge portion 705 discharging the hollow fiber membrane 31 and moving in an axial direction (arrow M1 direction in FIG. 9) of the main body portion 606. Moreover, the main body portion 606 is fixed to a linear table 608 and a ball nut member 704 moving on a linear rail 607. When a motor 703 is driven and a ball screw shaft 609 rotates, the ball nut member 704 can move in a manner parallel to the axial direction of the main body portion 606. The motor 703 can rotate normally and reversely and a controller (not illustrated) adjusts the driving thereof. Thus, the discharging of the hollow fiber membrane 31 occurs at a feeding point that traverses along a central axis direction of the cylinder 241 as the cylinder 241 rotates in order to perform a winding step.

The fixing device 600 is a device fixing the hollow fiber membrane 31 wound around the first cylinder member 241, using fixing strings (string-like bodies) 11. The fixing device 600 includes a first feeding mechanism 701A disposed on the right side, a second feeding mechanism 701B disposed on the left side, and a discharging mechanism 702.

The first feeding mechanism 701A is a mechanism feeding the fixing string 11 to the right end side in FIG. 9 (the same applies to FIG. 10) with respect to the discharging mechanism 702. In addition, the second feeding mechanism 701B is a mechanism feeding the fixing string 11 to the left end side in FIG. 9 with respect to the discharging mechanism 702. The first feeding mechanism 701A and the second feeding mechanism 701B have the same configuration except that disposed locations are different from each other. Therefore, hereinafter, the first feeding mechanism 701A will be representatively described.

The first feeding mechanism 701A has a support portion 708 rotatably supporting a bobbin 113 around which the fixing string 11 is wound in advance, a tensioner 709 applying a tensile force to the fixing string 11, a coil spring 801 biasing the tensioner 709, and a detection sensor 802 detecting the presence or absence of the fixing string 11.

The support portion 708 is disposed on the farthest upstream side in a transportation direction of the fixing string 11. Note that, the support portion 708 may rotate with the bobbin 113 or may be fixed.

The tensioner 709 is a roller disposed downstream in the transportation direction of the fixing string 11 with respect to the support portion 708. A tensile force can be applied to the fixing string 11 by winding a middle part of the fixing string 11 around the tensioner 709.

The coil spring 801 can bias a central portion of the tensioner 709 in the central axis direction thereof. The fixing string 11 oscillates while being fed and is likely to be loosened. However, the coil spring 801 biases the fixing string 11 together with the tensioner 709, so that a tensile force is reliably applied regardless of the degree of the oscillation thereof.

The detection sensor 802 is a sensor disposed downstream in the transportation direction of the fixing string 11 with respect to the tensioner 709, that is, disposed between the tensioner 709 and the discharging mechanism 702. The detection sensor 802 is not particularly limited. For example, a force sensor or the like can be used. For example, in a case where the fixing string 11 runs out or is unintentionally cut while fixing the hollow fiber membrane 31, this detection sensor 802 can reliably detect the state thereof.

The discharging mechanism 702 is a mechanism independently discharging the fixing string 11 fed from the first feeding mechanism 701A, and the fixing string 11 fed from the second feeding mechanism 701B toward the first cylinder member 241 on the core attachment member 605. The discharging mechanism 702 has a main body portion 706 individually pulling out (feeding) each of the fixing strings 11, and a discharge portion 707 individually discharging the fixing strings 11 toward both end portions of the first cylinder member 241. When the hollow fiber membrane 31 is fixed by using the fixing strings 11, the fixing strings 11 discharged from the discharge portion 707 are wound around the hollow fiber membrane 31 on the rotating first cylinder member 241, and the hollow fiber membrane 31 is fixed (refer to FIG. 11). After the hollow fiber membrane 31 is fixed, the fixing strings 11 adopted for the fixing are cut off from the fixing device 600 by using scissors or a cutter (not illustrated), for example. A cut portion of the fixing string 11 is fixed by using an adhesive tape or performing ultrasound welding, for example.

In this regard, for example, the fixing string 11 is formed of a flexible thermoplastic resin such as polyamide (e.g., nylon 6, nylon 46, nylon 66, nylon 610, nylon 612, nylon 11, nylon 12, nylon 6-12, nylon 6-66) or polyester (e.g., polyethylene terephthalate, polybutylene terephthalate, polyethylene naphthalate, polytributylene terephthalate). Accordingly, the hollow fiber membrane 31 can be fixed with a tensile force suitable for fixing. In addition, as the constituent material of the fixing string 11, in addition to a thermoplastic resin, a metal material such as stainless steel may be used.

Figure 11A:
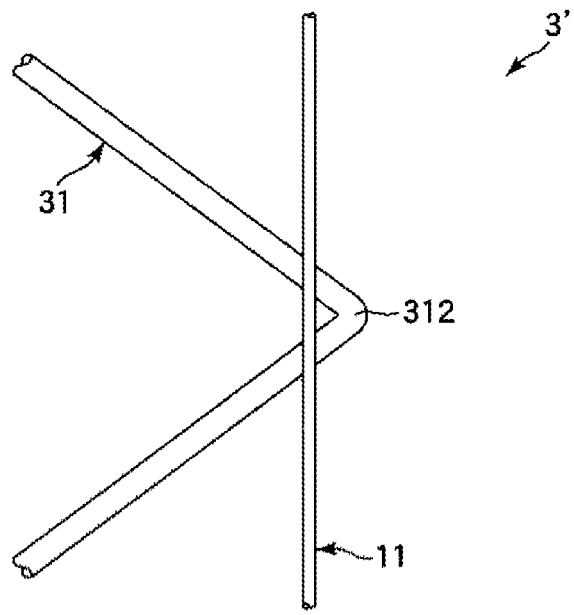
FIG. 11A and FIG. 11B are plan views illustrating a fixed state of a hollow fiber membrane during a process of manufacturing a hollow fiber membrane layer laminate.

In addition, as illustrated in FIG. 11, it is preferable that the outer diameter of the fixing string 11 is narrower than the outer diameter of the hollow fiber membrane 31. Accordingly, there is an advantage that even in a case where the number of windings increases, an increase in the outer diameters of both end portions of the base material 3' can be suppressed.

The first step is performed by using the winding apparatus 60 having a configuration as described above. Hereinafter, one hollow fiber membrane 31 will be representatively described.

As illustrated in FIGS. 7 to 10, in the first step, the feeding of hollow fiber membrane 31 is reciprocated in a central axis O direction while being wound around a central axis O of the first cylinder member 241 (cylinder). At this time, the hollow fiber membrane 31 starts to be wound from a start point 311 on the left side in the central axis O direction and is directed toward the right side. On the right side, the hollow fiber membrane 31 is turned back at a turning point (turned-back portion) 312. Thereafter, the hollow fiber membrane 31 returns to the left side again and reaches an end point 313.

Note that, in this specification, a value referred to as a winding ratio is defined as a value of 1 divided by the number of one way (end-to-end) traversals completed by the reciprocating motion during the time that the cylinder member 241 is wound by one complete round (i.e., spun 360° in a circumferential direction). The expression "wound by one complete round in the circumferential direction" indicates that the hollow fiber membrane 31 is wound from an upper side 300A to a lower side 300B, in the development views illustrated in FIGS. 7B, 8B, 13, and 14. In addition, the term "one way traversals" indicates that a hollow fiber starts to be wound from a left side 300C, reaches a right side 300D, and reaches the left side 300C again, in the development views illustrated in FIGS. 7B, 8B, 13, and 14.

For example, in the winding form illustrated in FIG. 7, the hollow fiber membrane 31 is wound in the order of arrows i→ii→iii→iv→v. In the winding form illustrated in FIG. 7, the hollow fiber membrane 31 reciprocates once in the central axis O direction while being wound one round in the circumferential direction, thereby resulting in the winding ratio=0.5. That is, when the winding ratio=0.5, the number of one ways becomes 2. In addition, in the winding form illustrated in FIG. 8, the hollow fiber membrane 31 is wound in the order of arrows i→ii→iii→iv→v→vi→vii. In the winding form illustrated in FIG. 8, the hollow fiber membrane 31 reciprocates 0.5 times in the central axis O direction while being wound one round in the circumferential direction, thereby resulting in the winding ratio=1. That is, when the winding ratio=1, the number of one ways becomes 1.

In addition, the hollow fiber membrane 31 reciprocates once via the start point 311, the turning point 312, and the end point 313, and its reciprocating is continuously repeated a plurality of times (refer to FIG. 13). Accordingly, a cylindrical hollow fiber membrane layer is formed, and a hollow fiber membrane layer laminate 3B (base material 3') constituted of a plurality of laminated hollow fiber membrane layers is formed. In addition, when the hollow fiber membrane 31 is continuously supplied to the first cylinder member 241, the hollow fiber membrane layer laminate 3B (base material 3') can be promptly manufactured, the manufacturing time can be shortened, and the cost can be minimized.

Figure 8A:
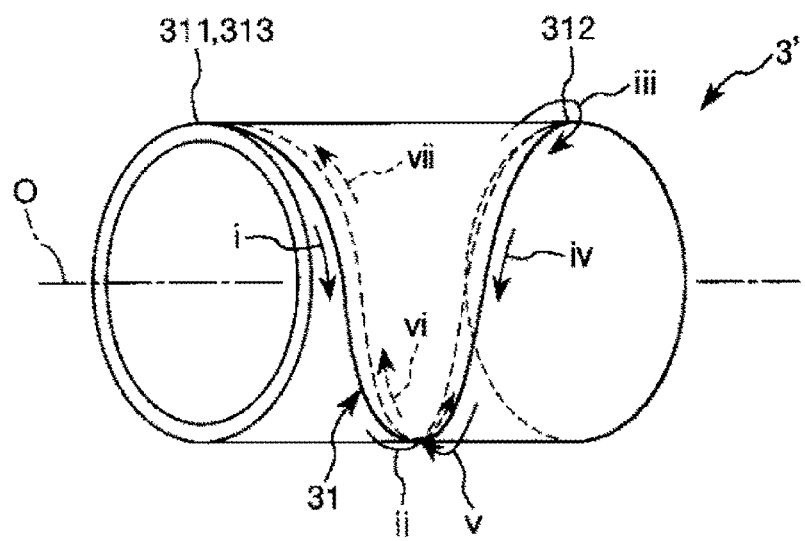
FIG. 8A is a perspective view and FIG. 8B is a development view illustrating another configuration of the hollow fiber membrane layer laminate manufactured by the method of manufacturing a hollow fiber membrane layer laminate of the present invention.
Figure 8B:
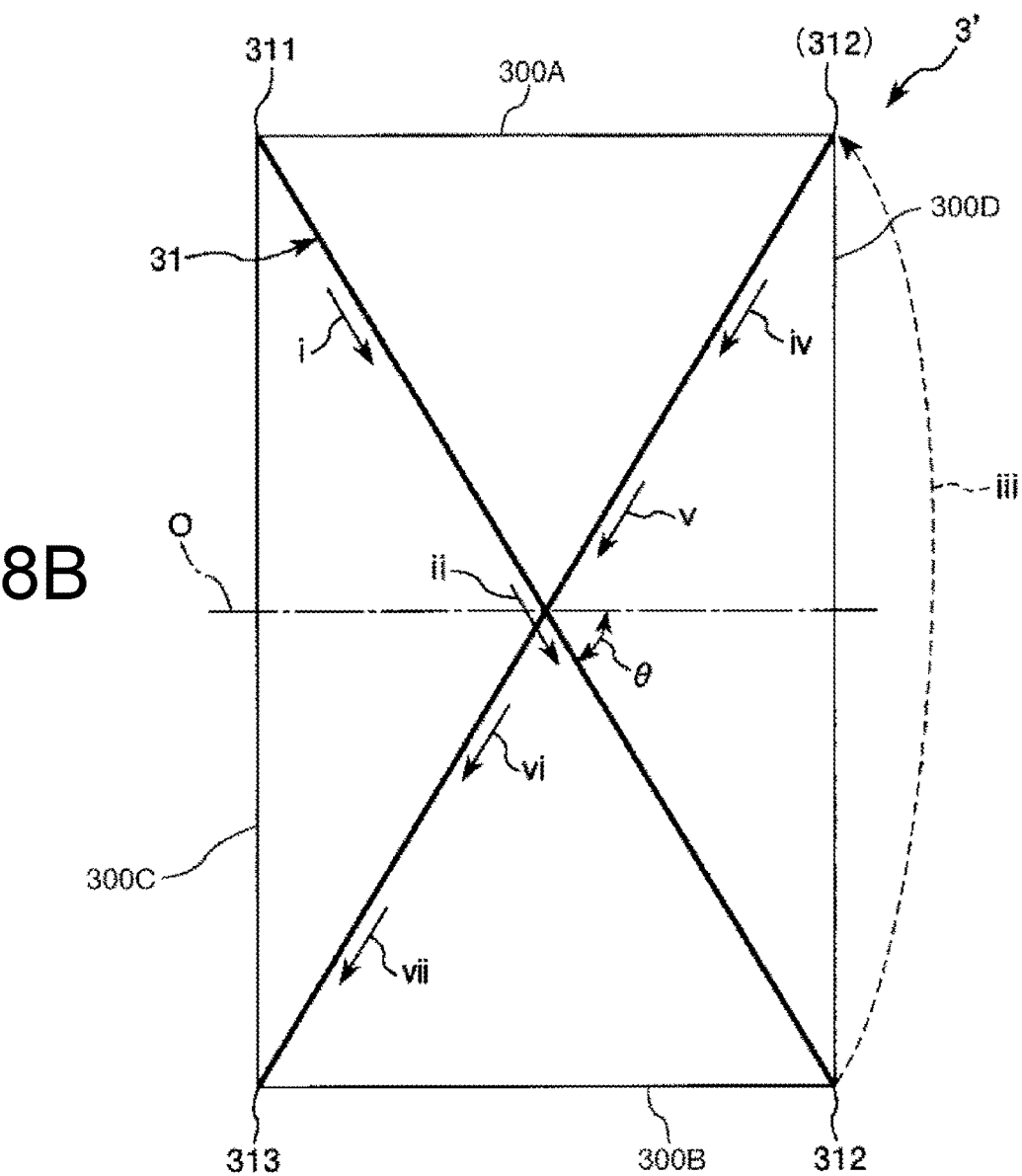

Note that, in FIGS. 7 and 8, for the sake of easy understanding, the case of the winding ratio=0.5 and the case of the winding ratio=1 are described as examples. However, in these cases, in order to prevent wound hollow fiber membranes 31 adjacent to each other from overlapping, a speed differential z is set such that the hollow fiber membranes 31 are actually separated from each other with a predetermined distance therebetween (i.e., spaced in the central axis O direction of the cylinder). Then, the separation distance between the hollow fiber membranes 31 adjacent to each other in the central axis O direction and the circumferential direction (which will hereinafter be simply referred to as "the separation distance") is determined. This will be described below in detail. Note that, the speed differential z is dependent upon a relationship between the longitudinal speed of the end-to-end traversals and the rotational speed of the cylinder which are adjusted to produce the desired separation distance, and wherein the speed differential z has a value obtained by dividing the distance (pitch) between the hollow fiber membranes adjacent to each other in the central axis O direction of the cylinder by an end-to-end traverse reciprocating distance.

In addition, in both the winding forms of FIGS. 7 and 8, the hollow fiber membrane 31 is tilted with respect to the central axis O at a tilt angle (lead angle) θ. When the tilt angle θ becomes smaller, the hollow fiber membrane 31 is required to be fixed at the turning point 312.

As illustrated in FIG. 11, every time the hollow fiber membrane 31 is turned back at the turning point 312, a spot in the vicinity of the turning point 312 is fixed. This fixing is performed by causing the fixing string 11 supplied from the fixing device 600 of the winding apparatus 60 to be wound around the central axis O and to be overlapped in the vicinity of the turning point 312. Accordingly, the hollow fiber membrane 31 is turned back at the turning point 312 regardless of the size of the tilt angle θ and is reliably wound in a stable manner. In addition, the winding state thereof is also maintained. Note that, as described below, this fixing string 11 remains without any change in the base material 3' but is removed in the hollow fiber membrane layer laminate 3B.

As described above, a tensile force is applied to the fixing string 11 by the tensioner 709. Accordingly, the fixing string 11 can fix the hollow fiber membrane 31 in a state where a tensile force acts. Such fixing contributes to moderate fixing of the hollow fiber membrane 31.

In addition, as illustrated in FIG. 11, in the first step, the hollow fiber membrane 31 is fixed with one fixing string 11 with respect to one turning point 312. Note that, the fixing form is not limited thereto. For example, depending on a string tensile force of the fixing string 11 to be wound, the hollow fiber membrane 31 can be fixed with a plurality of fixing strings 11 with respect to one turning point 312.

Figure 11B:
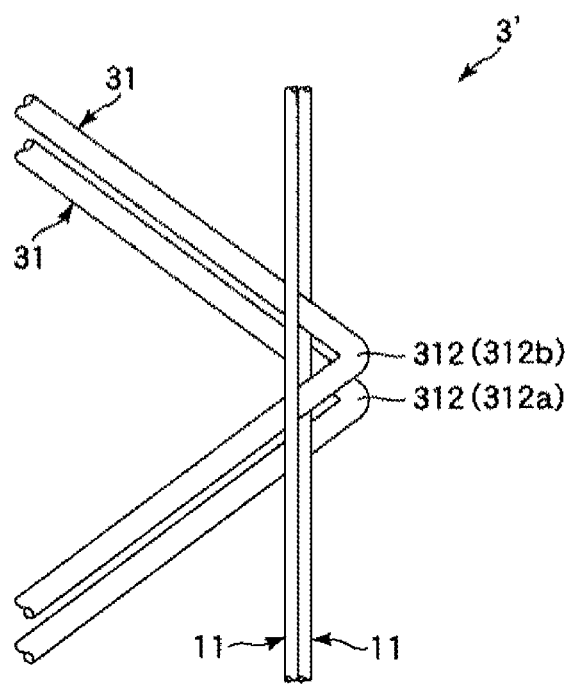

As illustrated in FIG. 10, in the winding apparatus 60, the first cylinder member 241 on the core attachment member 605 can move in the central axis O direction (arrow M2), so that the discharging mechanism 702 can move in the central axis O direction (arrow M3) while being interlocked (synchronized) with the movement thereof. Due to such a configuration, the base material 3' (hollow fiber membrane layer laminate 3B) in its entirety in the process of being manufactured can move in the central axis O direction, so that the fixing string 11 can follow the movement thereof (can traverse). Accordingly, for example, as illustrated in FIG. 11B, in a manner adjacent to the fixing string 11 fixing a leading turning point 312a, the fixing string 11 fixing a following turning point 312b can be disposed in parallel. Due to such disposition, the base material 3' can be prevented from gradually increasing in the outer diameters of both end portions thereof and forming a hand drum shape as a whole shape. That is, the base material 3' has a uniform outer diameter along the central axis O. In addition, an intersecting portion at which the hollow fiber membranes 31 intersect each other can also be prevented from overlapping another intersecting portion. Note that, in the winding apparatus 60, movement in the arrow M2 direction and the arrow M3 direction is independent from movement in the M1 direction.

In addition, the winding apparatus 60 is configured to use the fixing string 11 without cutting until manufacturing of the hollow fiber membrane layer laminate 3B is completed. Accordingly, for example, compared to a case where the fixing string 11 is cut every time one turning point 312 is fixed, the base material 3' can be promptly manufactured and the manufacturing time can be shortened.

In addition, in the first step, an adhesive may be applied to the turning point 312, or an adhesive tape may be pasted. Accordingly, fixing of the fixing string 11 can be assisted.

<Second Step (Winding Step)>

Figure 12A:
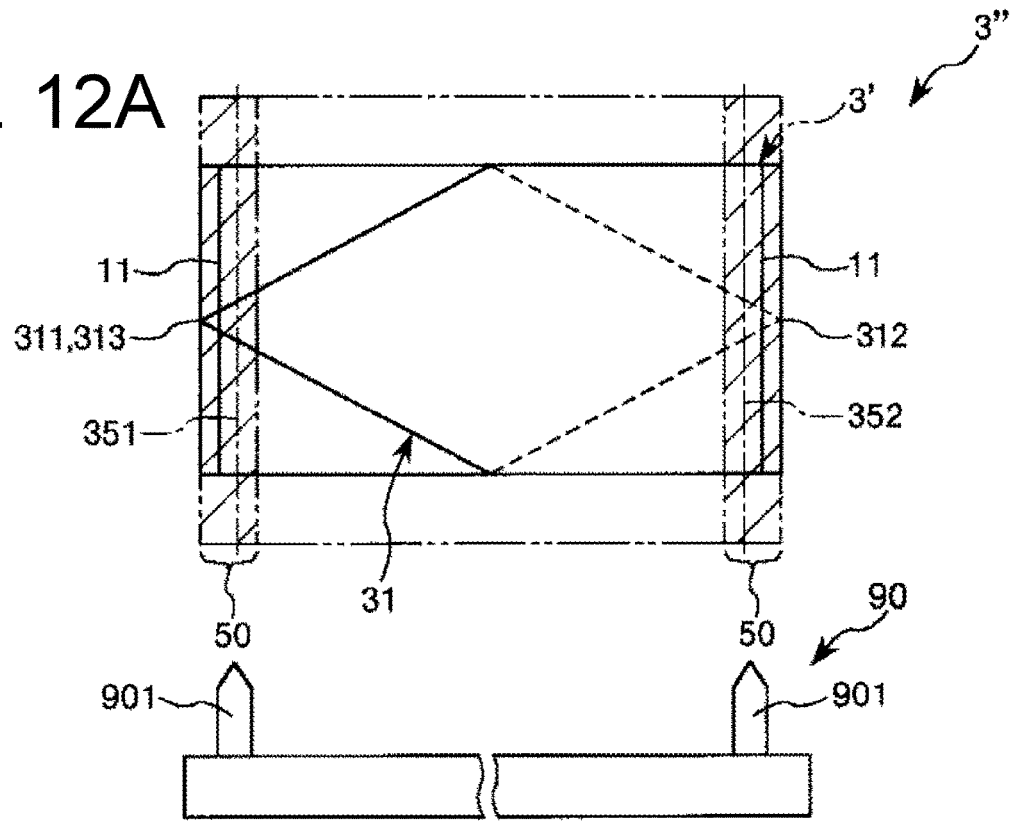
FIG. 12A and FIG. 12B are views sequentially illustrating a step of cutting a hollow fiber membrane bundle to remove a fixing string at each end.

The second step is a winding step of further winding the hollow fiber membrane 31, which becomes the hollow fiber membrane layer laminate 3A, on the base material 3'. Accordingly, a secondary base material 3" as illustrated in FIG. 12A is obtained.

In this second step, the winding apparatus 60 is used without any change, and the hollow fiber membrane 31 is wound in a winding form similar to that of the first step.

After the second step is completed, the secondary base material 3" is taken out from the winding apparatus 60 together with the first cylinder member 241.

<Third Step (Accommodating Step)>

The third step is an accommodation step of accommodating the secondary base material 3" in the cylindrical housing main body 21A together with the first cylinder member 241 after the filter member 41A is fixedly wound around the secondary base material 3".

Fourth Step (Fixing Step)>

The fourth step is a fixing step of fixing the secondary base material 3" to the cylindrical housing main body 21A. The secondary base material 3" is fixed by using a potting material 50, and the potting material 50 becomes the partition walls 8 and 9.

In order to perform this fixing, first, liquid polyurethane which is the constituent material of the potting material 50 is supplied toward both end portions of the secondary base material 3″ inside the cylindrical housing main body 21A. Next, the cylindrical housing main body 21A in its entirety is mounted in a centrifugal separator. Thereafter, the liquid polyurethane is dried. Accordingly, both end portions of the secondary base material 3″ are in a state of being fixed by the potting material 50 (refer to FIG. 12A). Note that, both end portions of the secondary base material 3″ also include the turning point 312, which is fixed by the fixing string 11 in the first step, the start point 311, and the end point 313.

<Fifth Step (Cutting Step)>

As illustrated in FIG. 12, the fifth step is a cutting step of individually cutting both end portions of the secondary base material 3″ fixed by the potting material 50. Accordingly, it is possible to collectively obtain the hollow fiber membrane layer laminate 3A and the hollow fiber membrane layer laminate 3B which are used in the oxygenator 10.

In this fifth step, a cutting apparatus 90 illustrated in FIG. 12 is used. The cutting apparatus 90 has two cutters (edged tools) 901. When each of the cutters 901 approaches the secondary base material 3″, both end portions of the secondary base material 3″ are cut. Note that, the cutting apparatus 90 is not limited to an apparatus configured to have the cutters 901. For example, an apparatus configured to jet a water jet or an apparatus configured to emit a laser beam may be adopted.

As illustrated in FIG. 12A, in the left end portion of the part fixed by the potting material 50 of the secondary base material 3″, a first cut line 351 is set in a part on the right side of the fixing string 11. In the right end portion as well, a second cut line 352 is set in a part on the left side of the fixing string 11.

Figure 12B:
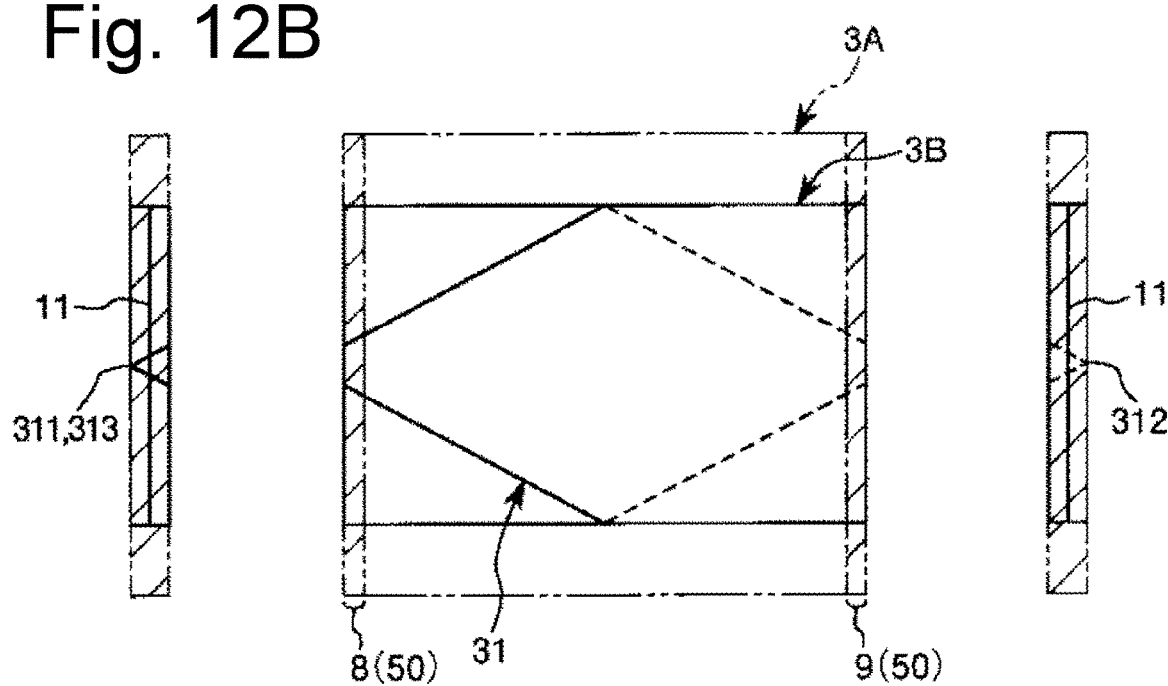

The secondary base material 3″ is cut along the first cut line 351 and the second cut line 352 by using the cutters 901 of the cutting apparatus 90. Accordingly, as illustrated in FIG. 12B, the secondary base material 3″ is divided into three members, and the member positioned at the center becomes the hollow fiber membrane layer laminate 3A and the hollow fiber membrane layer laminate 3B. Note that, the members at both ends are discarded.

In addition, due to this cutting, in the hollow fiber membrane layer laminate 3B (the same applies to the hollow fiber membrane layer laminate 3A), the turning point 312 is removed together with the fixing string 11. Accordingly, both ends of each of the hollow fiber membranes 31 constituting the hollow fiber membrane layer laminate 3B are open respectively, so that the heat medium H can pass through the inside of the hollow fiber membrane 31. Note that, in the hollow fiber membrane layer laminate 3A, the gas G can pass through the inside of each of the hollow fiber membranes 31.

<Sixth Step (Mounting Step)>

The sixth step is a mounting step of mounting each of the first lid 22A and the second lid 23A in the cylindrical housing main body 21A.

The oxygenator 10 can be obtained by performing such mounting. Note that, after mounting, for example, each of the first lid 22A and the second lid 23A may be fixed to the cylindrical housing main body 21A by using an adhesive or the like.

Figure 15A:
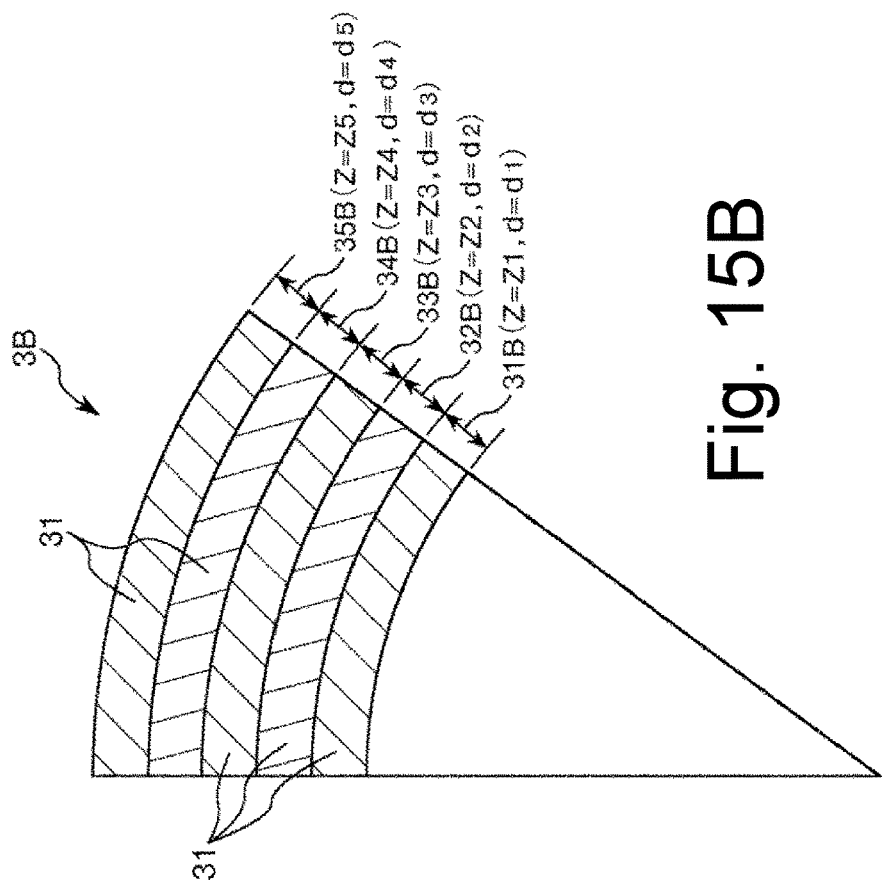
FIG. 15A and FIG. 15B are cross-sectional views of a part of a hollow fiber membrane layer laminate in the related art and in the present invention, respectively.
Figure 15B:
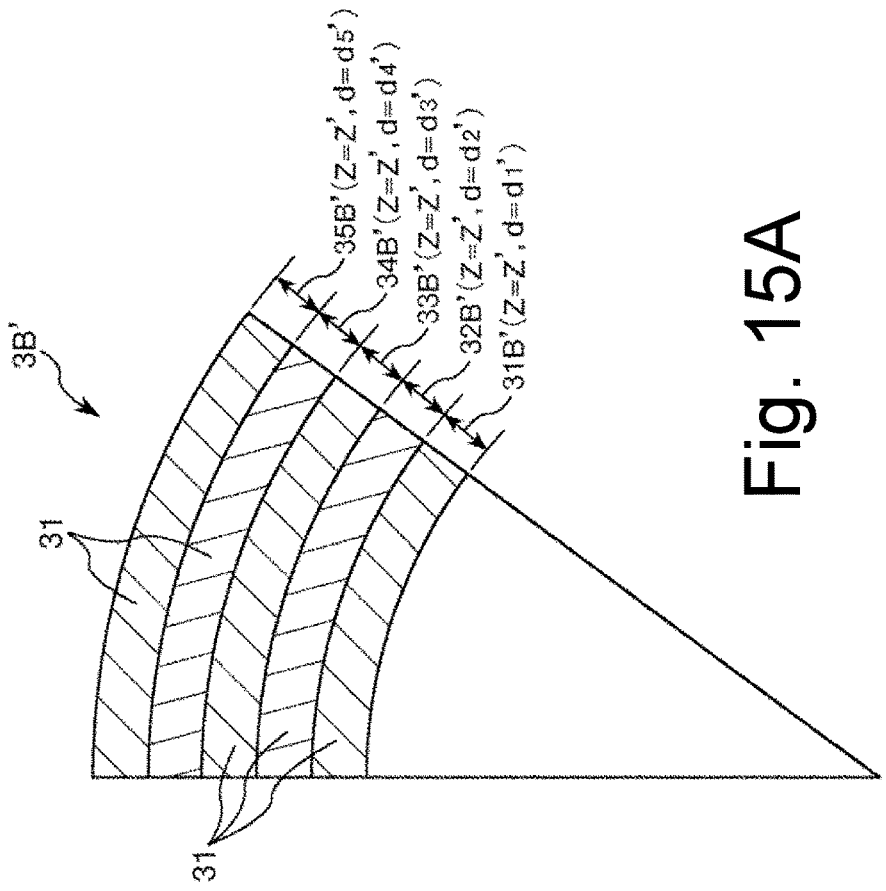

In hollow fiber membrane layer laminated bodies in the related art, even if the hollow fiber membranes 31 are wound at equal pitches, the separation distance d is gradually increased as the layer approaches the outer side in the radial direction of the cylinder. For example, as illustrated in FIG. 15B, in a case where the hollow fiber membrane layer laminate has a five-layer structure in which hollow fiber membrane layers 31B′, 32B′, 33B′, 34B′, and 35B′ are laminated in order from the inner side of the cylinder, the separation distance d2′ in the hollow fiber membrane layer 32B′ is longer than the separation distance d1′ in the hollow fiber membrane layer 31B′. In addition, the separation distance d3′ in the hollow fiber membrane layer 33B′ is longer than the separation distance d2′ in the hollow fiber membrane layer 32B′. The separation distance d4′ in the hollow fiber membrane layer 34B′ is longer than the separation distance d3′ in the hollow fiber membrane layer 33B′. The separation distance d5′ in the hollow fiber membrane layer 35B′ is longer than the separation distance d4′ in the hollow fiber membrane layer 34B′. In this manner, the separation distance d1′, the separation distance d2′, the separation distance d3′, the separation distance d4′, and the separation distance d5′ are gradually increased from the inner side in the radial direction of the cylinder to the outer side.

Note that, the aforementioned "pitch" indicates a distance between the central axes of the hollow fiber membrane 31 adjacent to each other in the central axis direction of the cylinder and is different from "the separation distance between the hollow fiber membranes 31". In addition, the aforementioned "separation distance" indicates the shortest distance between the longitudinal side edges of the hollow fiber membranes 31 adjacent to each other in the central axis direction and the circumferential direction of the cylinder and indicates a distance along a straight line orthogonal to the central axis of the hollow fiber membrane 31 (hereinafter, the same applies to the description). Note that, the separation distance is calculated by subtracting the sum of the lengths of the radii of the hollow fiber membranes adjacent to each other from the distance between the central axes of the hollow fiber membranes adjacent to each other. As described above, the separation distances d1′ to d5′ are gradually increased because the speed differential z is set to be uniform when the hollow fiber membrane layers 31B′ to 35B′ are formed. Hereinafter, this will be described in detail using the development view illustrated in FIG. 14.

First, as illustrated in FIG. 14A, the hollow fiber membrane 31 is wound at the speed differential z=z′. Note that, even when each of the hollow fiber membrane layers 32B′ to 35B′ is formed, the hollow fiber membrane 31 is wound at the speed differential z=z′. In a first round, the hollow fiber membrane 31 starts from a corner on the upper side 300A in the development view, is turned back in the middle of the right side 300D, is further turned back in the middle of the left side 300C, and reaches the lower side 300B. In a second round, on the upper side 300A, the distance from the left side 300C of an end point 313a′ in the first round starts from the same position. In a third round, on the upper side 300A, the distance from the left side 300C of an end point 313b′ in the second round starts from the same position. In this manner, the distance from the left side 300C of the end point 313a′ in the first round becomes a pitch P1′, and this P1′ is determined based on the speed differential z, which will be described below. In addition, the separation distance d1′ between the hollow fiber membranes in the hollow fiber membrane layer 31B′ is illustrated in FIG. 14A as the shortest distance between the hollow fiber membranes 31 adjacent to each other in the central axis direction and the circumferential direction of the cylinder and is derived by the Relational Expression (1) of the separation distance d and the pitch P, which will be described below.

Note that, the hollow fiber membrane layer 31B' is formed by performing winding in a fourth round and thereafter in a manner similar to that described above.

Next, the hollow fiber membrane layer 32B' is formed and laminated on the hollow fiber membrane layer 31B'. In addition, when the hollow fiber membrane layer 32B' is laminated, the hollow fiber membrane 31 is wound at the pitch=P2'. This P2' is the same as the P1'. The reason is that the hollow fiber membrane 31 is wound in the hollow fiber membrane layer 32B' at the speed differential z=z' similar to that of the hollow fiber membrane layer 31B'. At this time, as illustrated in FIG. 14B, the outer diameter of the cylinder (a target around which the hollow fiber membrane 31 is wound) increases as much as the amount wound on the hollow fiber membrane layer 31B'. That is, the left side 300C and the right side 300D in the development view become longer than those in FIG. 14A. Therefore, when the hollow fiber membrane 31 is wound at the speed differential z=z', the lead angle θ2' of hollow fiber membrane 31 for winding in the hollow fiber membrane layer 32B' becomes larger than the lead angle θ1' of the hollow fiber membrane 31 for winding in the hollow fiber membrane layer 31B'. As a result, the separation distance d2' in the hollow fiber membrane layer 32B' becomes longer than the separation distance d1' in the hollow fiber membrane layer 31B'.

Moreover, as illustrated in FIG. 14C, when the hollow fiber membrane layer 33B' is formed, similar to that described above, the lead angle θ3' of the hollow fiber membrane 31 for winding in the hollow fiber membrane layer 33B' becomes larger than the lead angle θ2' of hollow fiber membrane 31 for winding in the hollow fiber membrane layer 32B'. Thus, the separation distance d3' in the hollow fiber membrane layer 33B' becomes longer than the separation distance d2' in the hollow fiber membrane layer 32B'. Note that, when the hollow fiber membrane layer 33B' is laminated, the hollow fiber membrane 31 is wound at the pitch=P3'. This P3' is the same as the P1' and the P2'.

In this manner, the separation distance d1', the separation distance d2', the separation distance d3', the separation distance d4', and the separation distance d5' are gradually increased from the inner side in the radial direction of the cylinder to the outer side. The reason is that the following Expression (1) is established between the separation distance d and the pitch P:

$$d = P \times \sin θ - φ \qquad \text{Expression (1)}$$

Note that, P indicates the pitch, θ indicates the lead angle (the tilt angle of a hollow fiber membrane with respect to the central axis of the cylinder), and φ indicates the diameter of the hollow fiber membrane, respectively. The sign φ indicates the diameter of a hollow fiber membrane which is suitably selected to form a hollow fiber membrane layer laminate. That is, φ has a uniform value. As illustrated in FIG. 14, θ increases from the hollow fiber membrane layer on the inner side in the radial direction of the cylinder to the hollow fiber membrane layer on the outer side. Therefore, in a case where the pitch is set to be uniform, sin θ of the hollow fiber membrane layer 32B' becomes greater than sin θ of the hollow fiber membrane layer 31B'. Therefore, the separation distance d2' in the hollow fiber membrane layer 32B' becomes longer than the separation distance d1' in the hollow fiber membrane layer 31B'. Note that, the grounds for an increase in the separation distance d in a plurality of hollow fiber membrane layers laminated on the outer side of the hollow fiber membrane layer 32B' can also be described by using the foregoing Expression (1) in a similar manner.

Due to an increase in the separation distances d1' to d5', even if the separation distance d1' in the hollow fiber membrane layer 31B' provided in the innermost layer of the cylinder is set to be an optimal distance, the separation distance in each of the hollow fiber membrane layers on an outer layer of the hollow fiber membrane layer 31B' becomes longer than the optimal separation distance, as the layer approaches the outer side in the radial direction of the cylinder. In addition, if the separation distance d5' in the hollow fiber membrane layer 35B' provided in an outermost layer of the cylinder is intended to be set to be the optimal separation distance, then the separation distance in each of the hollow fiber membrane layers in an inner layer of the hollow fiber membrane layer 35B' becomes shorter than the optimal separation distance. In the former case, the blood loading amount increases, which increases the burden on a patient. Moreover, since the ratio of blood flowing without coming into contact with an outer surface of the heat exchange section increases, there is concern that sufficient heat exchange performance will not be able to be achieved. Meanwhile, in the latter case, air bubbles can remain between the hollow fiber membranes 31 adjacent to each other at the time of initial loading or the pressure loss in the blood flow path can be higher than necessary.

Above all, in a heat exchange section using a hollow fiber membrane layer laminate, it is known that the hollow fiber membrane layer laminate is disposed in an inner layer of an oxygenator section in which porous hollow fiber membranes are laminated. Accordingly, the inner diameter of the heat exchange section having a cylindrical shape becomes smaller than that of the oxygenator section. Therefore, when hollow fiber membrane layers having the same thickness are laminated, the rate of variation in the diameter of the heat exchange section in the radial direction becomes higher than the rate of variation in the diameter of the oxygenator section. Moreover, hollow fiber membranes used in a heat exchange section tend to have a larger diameter than hollow fiber membranes used in an oxygenator section. The reason is that since the heat medium circulating inside the hollow fiber membranes for a heat exchange section is liquid such as water, there is a need to further reduce the resistance in the flow path inside the hollow fiber membranes of the heat exchange section than the hollow fiber membranes of the oxygenator section for sending gas into the hollow fiber membranes. Accordingly, the difference between the separation distance d1' in the hollow fiber membrane layer 31B' and the separation distance d5' in the hollow fiber membrane layer 35B' becomes greater than that in the oxygenator section. That is, the foregoing disadvantage caused by the separation distance between hollow fiber membranes becoming shorter or longer than the optimal separation distance is particularly manifested in the heat exchange section. Accordingly, in the heat exchange section, in order to maintain the optimal separation distance between the hollow fiber membranes in each of the plurality of hollow fiber membrane layers laminated from the inner side in the radial direction of the cylinder to the outer side, the hollow fiber membrane has to be wound in consideration of characteristics of the heat exchange section, and there is a need to perform control more accurately than the method of winding the hollow fiber membrane in the oxygenator section.

According to the present invention, such a disadvantage can be advantageously prevented particularly in the heat exchange section. Hereinafter, this will be described with reference to FIGS. 13A to 13C. Note that, the hollow fiber membrane layer laminate 3B formed by the method described below has a five-layer structure in which a hollow fiber membrane layer 31B, a hollow fiber membrane layer 32B, a hollow fiber membrane layer 33B, a hollow fiber membrane layer 34B, and a hollow fiber membrane layer 35B are laminated from the from the inner side in the radial direction of the cylinder to the outer side.

First, as illustrated in FIG. 13A, the hollow fiber membrane 31 is wound at the speed differential z=z1. In the first round, the hollow fiber membrane 31 starts from the left corner on the upper side 300A in the development view, is turned back in the middle of the right side 300D, is further turned back in the middle of the left side 300C, and reaches the lower side 300B. In the second round, on the upper side 300A, the distance from the left side 300C of an endpoint 313a in the first round starts from the same position. In the third round, on the upper side 300A, the distance from the left side 300C of an end point 313b in the second round starts from the same position. In this manner, the distance from the left side 300C of the end point 313a in the first round becomes a pitch P1, and this pitch P1 is determined based on the speed differential z. That is, the pitch P(N) can be expressed by the following Expression (2):

Pitch=2*TXz*                                      Expression(2)

Note that, TX indicates a reciprocating width, that is, the sum of lengths of the upper side 300A and the lower side 300B in FIGS. 13A to 13C.

The hollow fiber membrane layer 31B is formed by performing winding in the fourth round and thereafter in a manner similar to that described above.

Next, as illustrated in FIG. 13B, the hollow fiber membrane 31 is wound on the hollow fiber membrane layer 31B, so that the hollow fiber membrane layer 32B is formed and laminated. At this time, similar to that described above, as illustrated in FIG. 13B, the outer diameter of the cylinder (a target around which the hollow fiber membrane 31 is wound) increases as much as the amount wound on the hollow fiber membrane layer 31B. That is, the left side 300C and the right side 300D in the development view become longer than those in FIG. 13A. Here, in the present invention, when the hollow fiber membrane layer 32B is formed, winding is performed by setting the speed differential z to a speed differential z2 smaller than a speed differential z1. Accordingly, regardless of the left side 300C and the right side 300D in the development view becoming longer than those in FIG. 13A, the position of an end point 313c in the first round can be on the left side of the position of the endpoint 313a in the first round in the diagram when the hollow fiber membrane layer 31B is formed. Thus, the position of a start point 313d in the second round can be on the left side of the position of a start point 313e in the second round in the diagram when the hollow fiber membrane layer 31B is formed. As a result, a pitch P2 becomes smaller than the pitch P1. The same applies to the third round and thereafter.

Next, as illustrated in FIG. 13C, the hollow fiber membrane 31 is wound on the hollow fiber membrane layer 32B, so that the hollow fiber membrane layer 33B is formed and laminated. At this time, similar to that described above, as illustrated in FIG. 13C, the outer diameter of the cylinder (a target around which the hollow fiber membrane 31 is wound) increases as much as the amount wound on the hollow fiber membrane layer 32B. That is, the left side 300C and the right side 300D the development view become longer than those in FIG. 13B. In the present invention, when the hollow fiber membrane layer 33B is formed, winding is performed by setting the absolute value z of the speed differential to a speed differential z3 smaller than the speed differential z2. Accordingly, regardless of the left side 300C and the right side 300D in the development view becoming longer than those in FIG. 13B, the position of an end point 313f in the first round can be on the left side of the position of the end point 313c in the first round when the hollow fiber membrane layer 32B is formed. Thus, the position of a start point 313g in the second round can be on the left side of the position of the start point 313d in the second round in the diagram when the hollow fiber membrane layer 32B is formed. As a result, a pitch P3 becomes smaller than the pitch P2. The same applies to the third round and thereafter.

Note that, when the hollow fiber membrane layer 34B is formed, the speed differential z is set to a speed differential z4 smaller than the speed differential z3, and when the hollow fiber membrane layer 35B is formed, the absolute value z of the speed differential is set to a speed differential z5 smaller than the speed differential z4 (not illustrated).

Thus, in accordance with the outer diameter of the cylinder (a winding target) gradually increasing as the hollow fiber membrane layer approaches the outer side in the radial direction of the cylinder, the absolute value z of the speed differential of the hollow fiber membrane layers is reduced. Accordingly, the pitch can be reduced as the layer approaches the outer side. This means that the change in the separation distance d between the hollow fiber membrane layers obtained by Expression (1) can be minimized in the layers from the inner to outer side in the radial direction of the cylinder by reducing the pitch against the increase in the lead angles θ1, θ2, and θ3 of the hollow fiber membrane layers from the inner to outer side in the radial direction of the cylinder. Thus, the separation distance between the hollow fiber membranes 31 can be prevented from being increasing as the hollow fiber membrane layer approaches the outer side in the radial direction of the cylinder, in contrast to the related art. Thus, as illustrated in FIG. 15B, the separation distances d1 to d5 can be substantially the same as each other. As a result, as described above, a load to a patient can be prevented from being increased due to the increased blood loading amount, and a state where air bubbles remain between the hollow fiber membrane 31 adjacent to each other can be prevented.

Such speed differentials z1 to z5 can be determined by using the following Expressions (3) and (4).

The first layer, that is, the separation distance d1 in the hollow fiber membrane layer 31B can be expressed by the following Expression (3):

$$d = 2zTX\left\{\frac{\pi D}{\sqrt{(2(z+1)TX)^2 + (\pi D)^2}}\right\} - \phi \quad (3)$$

Note that, TX indicates the reciprocating width, that is, the lengths of the upper side 300A and the lower side 300B in FIGS. 13A to 13C. The sign D indicates the diameter of the cylinder for winding. The sign φ indicates the outer diameter (φd1) of the hollow fiber membrane 31.

In addition, the separation distance d(N) in an Nth hollow fiber membrane layer (N is a positive integer) can be expressed by the following Expression (4).

$$d(N) = 2zTX\left[\frac{\pi(D + 2(N-1)\phi)}{\sqrt{(2(z+1)TX)^2 + \{\pi(D + 2(N-1)\phi)\}^2}}\right] - \phi \quad (4)$$

Note that, N indicates the total number of wound layers. For example, when the hollow fiber membrane layer 31B is formed, N=0 is established, and when the hollow fiber membrane layer 32B is formed, N=1 is established.

In a case of assumption that d=d(N) is established, the speed differential z is derived based on Expressions (3) and (4), that is, the speed differentials z1 to z5 are determined. For example, the speed differential z1 is derived by substituting N=0, and the speed differential z2 is derived by substituting N=1.

Note that, it is preferable the speed differentials z1 to z5 are reduced at a uniform ratio, that is, reduced at a uniform decrement rate. Accordingly, the variation in the separation distances d1 to d5 can be effectively reduced, and the advantageous effects of the present invention can be reliably achieved.

In addition, the decrement rate of the speed differential z, that is, a difference Δz of the speed differentials z in two hollow fiber membrane layers adjacent to each other in the radial direction of the cylinder is preferably within a range of 0.4% to 1.1% of the speed differential z of the hollow fiber membrane layer on the inner side and is more preferably within a range of 0.4% to 0.5%. Accordingly, the variation in the separation distances d1 to d5 can be effectively reduced, and the advantageous effects of the present invention can be reliably achieved.

In the hollow fiber membrane layer laminate 3B obtained by the manufacturing method as described above, the separation distances d1 to d5 may be the same as each other or may be different from each other. However, the advantageous effects of the present invention can be achieved when the rate of variation in the separation distance between hollow fiber membranes adjacent to each other in the central axis direction and the circumferential direction of the cylinder is 20% or less from the innermost to outermost layer in the hollow fiber membrane layer laminate 3B. Specifically, the ratio d1/d2 between the separation distances d1 and d2, the ratio d1/d3 between the separation distances d1 and d3, the ratio d1/d4 between the separation distances d1 and d4, and the ratio d1/d5 between the separation distances d1 and d5 may be only in the range of 0.8 to 1.2. When the separation distances satisfy the foregoing conditions, the separation distance between hollow fiber membranes adjacent to each other in the circumferential direction of the cylinder in the hollow fiber membrane layer provided in the innermost layer of the cylinder can have substantially the same ratio to the separation distances between hollow fiber membranes adjacent to each other in the circumferential direction of the cylinder in a plurality of hollow fiber membrane layers laminated outside, in the radial direction of the cylinder, the hollow fiber membrane layer provided in the innermost layer.

Accordingly, with respect to the heat exchange section in which the difference between the separation distances between hollow fiber membranes in each of the innermost layer and the outermost layer of the hollow fiber membrane layer laminate becomes larger than that in the oxygenator, the separation distance between hollow fiber membranes adjacent to each other in the central axis direction and the circumferential direction of the cylinder throughout the hollow fiber membrane layer laminate 3B from the innermost layer to the outermost layer can be set within a range of 0.8 times to 1.2 times of an optimal value. Therefore, the blood loading amount, the heat exchange performance, and a pressure loss in the blood flow path can be properly retained, and remaining air bubbles can be reliably reduced.

In addition, in the description above, the first step, that is, a step of manufacturing the hollow fiber membrane layer laminate 3B has been representatively described. However, it is needless to mention that the present invention can also be applied to the second step, that is, a step of manufacturing the hollow fiber membrane layer laminate 3A. According to the present invention, the separation distance between hollow fiber membranes can be prevented from excessively increasing as the hollow fiber membrane layer approaches the outer side of the cylinder, in contrast to the related art. Thus, a load to a patient can be prevented from being increased due to the increased blood loading amount as described above in regard to the oxygenator section constituting the hollow fiber membrane layer laminate 3A.

Note that, in the description above, a hollow fiber membrane layer laminate having a five-layer structure has been described as an example. However, it is needless to mention that the present invention can also be applied to a structure of two to four layers or a structure of six or more layers.

Hereinabove, the method of manufacturing a hollow fiber membrane layer laminate of the present invention and the hollow fiber membrane layer laminate have been described based on the illustrated embodiment. However, the present invention is not limited thereto. The method of manufacturing a hollow fiber membrane layer laminate of the present invention and the hollow fiber membrane layer laminate may include any optional step.

In addition, each of the hollow fiber membranes constituting the hollow fiber membrane layer laminate of the oxygenator section and each of the hollow fiber membranes constituting the hollow fiber membrane layer laminate of the heat exchange section have been the same as each other in the embodiment. However, the embodiment is not limited thereto. For example, hollow fiber membranes on one side (the former case) may be thinner than hollow fiber membranes on the other side (the latter case), or the hollow fiber membranes of both thereof may be formed of materials different from each other.

In addition, in regard to the oxygenator section and the heat exchange section, in the embodiment, the heat exchange section is disposed on the inner side and the oxygenator section is disposed on the outer side. However, the embodiment is not limited thereto. The oxygenator section may be disposed on the inner side and the heat exchange section disposed on the outer side. In this case, blood flows down from the outer side to the inner side.

What is claimed is:

1. A method of manufacturing a hollow fiber membrane layer laminate comprised of a plurality of hollow fiber membranes forming a cylinder, the method comprising:

winding the hollow fiber membranes around a central axis of the cylinder while reciprocating a feeding point of the hollow fiber membranes in a central axis direction of the cylinder to laminate a plurality of hollow fiber membrane layers in a radial direction of the cylinder, wherein the hollow fiber membranes adjacent to each other within each layer are separated by a predetermined separation distance; and reducing a speed differential z of the winding of the hollow fiber membranes for successive layers as the winding step approaches an outer side in the radial direction of the cylinder, wherein the speed differential z has a value obtained by dividing a pitch of the hollow fiber membranes within each respective layer of the cylinder by a traverse reciprocating distance of the cylinder;

wherein the hollow fiber membrane layers include an innermost first layer with a first speed differential z1 and a first separation distance d1 and a plurality of radially overlying layers each with a respective speed differential z and a respective separation distance d; and wherein a respective ratio of d1 to each respective overlying separation distance d is within a range from 0.8 to 1.2.

2. The method of manufacturing a hollow fiber membrane layer laminate according to claim 1:

wherein a difference between the speed differentials z in the hollow fiber membrane layers adjacent to each other in the radial direction of the cylinder is within a range of 0.4% to 1.1%.

3. The method of manufacturing a hollow fiber membrane layer laminate according to claim 1 wherein the reduction of the speed differential z is a gradual reduction according to an increasing diameter of the cylinder, thereby providing a gradual increase of the pitch and reducing a variation of the separation distance d.

4. A hollow fiber membrane layer laminate for an oxygenator, comprising:

a plurality of hollow fiber membranes wound into a cylinder:

wherein the plurality of hollow fiber membranes form a laminate having a plurality of layers in a radial direction of the cylinder;

wherein the plurality of hollow fiber membranes within each respective layer are separated from each other by a predetermined separation distance; and wherein a pitch of the hollow fiber membranes is successively reduced from an innermost layer of the cylinder to an outermost layer of the cylinder so that the predetermined separation distance is maintained throughout the layers;

wherein the layers include an innermost first layer with a first separation distance d1 and a plurality of radially overlying layers each with a respective separation distance d; and wherein a respective ratio of d1 to each respective overlying separation distance d is within a range from 0.8 to 1.2.

5. The hollow fiber membrane layer laminate according to claim 4:

wherein the predetermined separation distance is from 50 μm to 300 μm.

6. The hollow fiber membrane layer laminate according to claim 4:

wherein the hollow fiber membranes have an outer diameter of 300 μm to 1,000 μm.

7. The hollow fiber membrane layer laminate according to claim 4 comprising a heat exchanger in which a heat medium passes through inside the hollow fiber membranes.

8. A hollow fiber membrane layer laminate for an oxygenator, comprising:

a plurality of hollow fiber membranes wound into a cylinder;

wherein the plurality of hollow fiber membranes form a laminate having a plurality of layers in a radial direction of the cylinder;

wherein the plurality of hollow fiber membranes within each respective layer are separated from each other by a separation distance; and wherein a variation in the separation distance between successive layers is 20% or less in comparison with an innermost layer.

* * * * *